United States Patent
Litt et al.

(10) Patent No.: US 6,635,469 B1
(45) Date of Patent: *Oct. 21, 2003

(54) PRESSURE-MEDIATED BINDING OF BIOMOLECULAR COMPLEXES

(75) Inventors: Gerald J. Litt, Centerville, MA (US); James A. Laugharn, Winchester, MA (US); David J. Green, Fitzwilliam, NH (US)

(73) Assignee: BBI Bioseq, Inc., West Bridgewater, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/214,250

(22) PCT Filed: Jul. 1, 1997

(86) PCT No.: PCT/US97/11198

§ 371 (c)(1), (2), (4) Date: Aug. 20, 1999

(87) PCT Pub. No.: WO98/00032

PCT Pub. Date: Jan. 8, 1998

Related U.S. Application Data

(60) Provisional application No. 60/044,595, filed on Apr. 22, 1997, and provisional application No. 60/020,562, filed on Jul. 2, 1996.

(51) Int. Cl.[7] ............................................. G01N 33/53
(52) U.S. Cl. ........................ 435/287.1; 435/4; 435/5; 435/7.1; 436/501; 436/506; 436/507; 436/536; 436/538; 436/543
(58) Field of Search .................. 435/4, 5, 7.1, 287.1; 436/501, 506, 507, 536, 538, 543; 530/412, 427

(56) References Cited

U.S. PATENT DOCUMENTS

| | | | |
|---|---|---|---|
| 4,656,251 A | 4/1987 | Mosier | 530/387 |
| 4,732,683 A | 3/1988 | Georgiades et al. | 210/635 |
| 4,753,775 A | 6/1988 | Ebersole et al. | 422/81 |
| 5,003,047 A | 3/1991 | Yarmush et al. | 530/413 |
| 5,011,608 A | 4/1991 | Damjanovic | 210/656 |

FOREIGN PATENT DOCUMENTS

| | | | |
|---|---|---|---|
| EP | 0 141 547 A1 | 5/1985 | G01N/33/537 |
| WO | WO 90/00251 | 1/1990 | G01N/33/78 |

OTHER PUBLICATIONS

Nuttall et al. (1986). False–positive results with HIV ELSA kits. Lancet. Aug. 30, 1986, pp. 512–513.*

(List continued on next page.)

*Primary Examiner*—Christopher L. Chin
(74) *Attorney, Agent, or Firm*—Fish & Richardson P.C.

(57) ABSTRACT

The invention relates to (1) pressure-mediated dissociation of an analyte complexed with an endogenous binding partner to enable detection of a complex formed from the analyte and an exogenous binding factor, (2) pressure-mediated association of an analyte and an exogenous binding partner to enable more rapid and/or more sensitive detection of an analyte, and (3) pressure-mediated association and dissociation of biomolecular complexes to enable separation of one biomolecule from a complex mixture. Pressure can be used to improve assays by dissociating endogenous analyte complexes and improving assay speed and sensitivity by associating the analyte molecules with exogenously supplied binding partners. Pressure can also be used to improve the separation of compounds from contaminated mixtures.

Methods of assaying an analyte in a sample having an endogenous complex between the analyte and an endogenous sample component include dissociating the analyte from the endogenous component using pressure and reacting the analyte with an exogenously supplied specific binding reagent to determine complexation between the analyte and the binding reagent.

22 Claims, 7 Drawing Sheets

OTHER PUBLICATIONS

Christiansen et al. (1996). False negative anti–HIV–1/HIV–2 ELISAs in acute HIV–2 infection. Vox Sang. 70:144–147.*

Craske et al. (1990). Comparison of false–positive reactions in derect–binding anti–HIV ELISA using cell lysate of recombinant antigens. Vox Sang. 59:160–166.*

McAlpine et al. (1995) False negative results in enzyme linked immunosorbent assays using synthetic HIV antigens. J. Clin. Pathol. 48:490–493.*

Komblatt et al. (1992). Cytochrome c and cytochrome c ixidase interactions: the effects of ionic strength and hydrostatic pressure studied with site–specific modifications of cytochrome c. Biochem. cell Biol. 70:539–547.*

Taube et al. (1990). Mechanism of ligand binding to heme and hemoproteins. A high pressure study. J. Am. Chem. Soc. 112:6880–6886.*

Van der Groen et al. (1987). Innunofluorescence tests for HIV antibody and their value as confirmatory tests. J. Virological Meth. 17:35–43.*

Grob et al. (1990). Pressure–induced dssociation of tight couple ribosomes. FEBS. 267(2):239–241.*

Muller et al. (1984). High pressure dissociation of lactate dehydrogenase from bacillus stearothermophilus and reconstitution of enzyme after denatureation in 6M guanidine hydrochloride. Eur. Biophys. J. 11:87–94.*

Thorell et al., "Separation Techniques" and "Assay Performance", Radioimmunoassay and related techniques, C.V. Mosby, St. Louis, (1978), pp. 50–74.

Lau et al., "Measurement of Serum Vitamin $B_{12}$ Level Using Radioisotope Dilution and Coated Charcoal", Blood: vol. 26, No. 2, (Aug. 1965), pp. 202–214.

Lilja et al., "Prostate–Specific Antigen in Serum Occurs Predominantly in Complex with α–Antichymotrypsin", Clin. Chem., vol. 37, No. 9, (1991), pp. 1618–1625.

Gourevitch et al., "Polymorphic epithelial mucin (MUC–1)–containing circulating immune complexes in carcinoma patients", Br. J. Cancer, vol. 72, No. 4, (1995), pp. 934–938.

Hilgers et al., "Quantitation of polymorphic epithelial mucin: a challenge for biochemists and immunologists" The Scand. J. Clin. Lab. Invest., vol. 55, Suppl. 220, (1995), pp. 81–86.

Tsiquaye et al., "Restriction of sensitivity of HIV–1–antigen ELISA by serum anti–core antibodies", AIDS, vol. 2, No. 1, 1988, pp. 41–45.

McHugh et al., "Relation of Circulating Levels of Human Immunodeficiency Virus (HIV) Antigen, Antibody to p24, and HIV–Continaing Immune Complexes . . . ", J. Infect. Dis., vol. 158, No. 5, (Nov. 1988), pp. 1088–1091.

Nishanian et al., "A Simple Method for Improved Assay Demonstrates that HIV p24 Antigen is Present as Immune Complexes in Most Sera from HIV–Infected . . . ", J. Infect. Dis., vol. 162, No. 1, (Jul. 1990), pp. 21–28.

Carini et al., "Characterization of Specific Immune Complexes in HIV–Related Disorders", Scand. J. Immuno., vol. 26, Nos. 1–6, (1987), pp. 21–28.

Wesierska–Gadek et al., "Autoantibodies Against Different Histone H1 Subtypes in Systemic Lupus Erythematosus Sera", Arthritis & Rheumatism, vol. 33, No. 8, (Aug. 1990), pp. 1273–1278.

Dlugovitzky et al., "Circulating immune complexes in patients with advanced tuberculosis and their association with autoantibodies and reduced . . . ", Braz. J. Med. Biol. Res., vol. 28 (1995), pp. 331–335.

Tsai et al., "Clinical evaluation of serum α–fetoprotein and circulating immune complexes as tumour markers of hepatocellular carcinoma", Br. J. Cancer, vol. 72, No. 2, (Aug. 1995), pp. 442–446.

Didenko et al., "Ultrastructure of circulating immune complexes isolated from the blood plasma of patients suffering from infectious diseases", J. Basic Microbiol., vol. 35, (1995), pp. 163–170.

Sinha et al., "Analysis of Circulating Immune Complexes from Leprosy Patients for *Mycobacterium leprae* Antigens", Int. J. Lepr., vol. 60, No. 3, (1992), pp. 396–403.

Weil et al., "Monoclonal Antibodies to Parasite Antigens Found in the Serum of Dirofilaria Immitis–Infected Dogs", J. Immunology, vol. 134, No. 2, (Feb. 1985), pp. 1185–1191.

Olson et al., "Recovery of Antigens from Immunoadsorbents Using High Pressure", Biotechnology, vol. 7, (Apr. 1989), pp. 369–373.

Howlett et al., "Pressure–induced conformational changes in an antigen and an antibody and the implications on their use for hyperbaric . . . ", Biochimica et Biophysica Acta, vol. 1159, No. 3, (1992), pp 227–236.

Gross et al., "Proteins Under Pressure: The Influence of High Hydrostatic Pressure on Structure, Function and Assembly of Proteins and Protein Complexes", Eur. J. Biochem., (1994), vol. 221. pp. 617–630.

Sundaram et al., "Engineering and Analysis of Pressure Sensitive Antibodies", J. Cell. Biochem., (1994), vol. Suppl. 18D, p. 209, Abstract No. T 413.

Cerrero and Voss, "Temperature and pH . . . Fluorescein Binding within . . . as Monitored by Hydrostatic Pressure", The Journal of Biological Chemistry, vol. 271, No. 10, Issue of Mar. 8, pp. 5332–5337, 1996.

Coelho–Sampaio and Voss, "Pressure–Induced Dissociation of Fluorescein from the Anti–Fluorescein Single–Chain Antibody 4–4–20", Biochemistry, vol. 32, No. 41, pp. 10929–10935, Oct. 19, 1993.

Yarmush et al., "Immunoadsorption: Strategies for Antigen Elution and Production of Resable Adsorbents", BioTechnology Progress, vol. 8, No. 3, pp. 168–178, May/Jun. 1992.

Degraeve and Lemay, "Antigen–Antibody Interactions . . . a Baro–Immunodesorption Process", High Pressure Research In The Biosciences and Biothechnology, K. Heremans (Ed.), Leuven university Press, Leuven, Belgium, pp. 115–118, Sep. 1–5, 1996.

Herron et al., "Thermodynamic Properties of Ligand Binding by Monoclonal Anti–fluorescyl Antibodies", Biochemistry, vol. 25, No. 16, pp. 4602–4609, Aug. 12, 1986.

Campbell and Johnson, "Pressure and Specific Precipitation", The Journal of the American Chemical Society, Communications To The Editor, vol. 68, p. 725, Apr. 1946.

Tsuji et al., "The Effect of Hydrostatic Pressure . . . Of Cypridina Luciferase By Specific Antibody", The Journal of Immunology, vol. 96, No. 4, pp. 614–621, 1966.

Sundaram et al., "Pressure–Induced Dissociation of Antigen–Antibody Complexes", Biotechnol. Prog. vol. 14, No. 5, pp 773–781, Sep./Oct. 1998.

Degraeve et al., "Pressure–induced inactivation of E. Coli β–galactosidase: influence of pH and temperature", Biochimica et Biophysica Acta, vol. 1292, No. 1, pp 61–68, Jan. 4, 1996.

* cited by examiner

PRESSURE-MEDIATED BINDING OF BIOMOLECULAR COMPLEXES

This application is a 371 of PCT/US97/11198 filed Jul. 1, 1997, which claims benefit of Provisional No. 60/044,595 filed Apr. 22, 1997, which claims benefit of Provisional No. 60/020,563 filed Jul. 2, 1996.

FIELD OF THE INVENTION

The invention is in the general field of analyte detection, assays, and methods for the separation of particular compounds from a mixture.

BACKGROUND OF THE INVENTION

Assays of Biomolecules: Assays can be used to determine whether, and how much of, an analyte is present in a sample. In some cases, such assays rely on selective binding or complexation (specific or nonspecific) of the analyte in the sample with an exogenously supplied capture reagent or binding partner.

Effects of endogenous binding partners on assays: Often such samples contain an endogenous component that forms a complex with the analyte, and the resulting endogenous complex may interfere with detection of the analyte. For example, detection by absorbance, fluorescence, molecular weight, or other analyte characteristics may be adversely affected by endogenous complexes. Where detection itself depends on formation of a complex with an exogenously supplied reagent, analyte present in endogenous complexes may be unable to effectively complex with the exogenous binding partner (as is required for detection in such assays). In that way, the endogenous complex interferes with the assay's reliability. For example, the analyte goes undetected or is incompletely detected—i.e., it provides a false negative or non-quantitative result.

This problem can be illustrated with standard enzyme-linked immunosorbent assays (ELISAs), in which sample antigen is detected only if it is recognized and bindable by immobilized antibody. Endogenous sample antibodies that react with the analyte may prevent at least some portion of the analyte from complexing with one or both of the exogenous assay reagents (antibodies), thereby reducing the effectiveness of the assay.

Assays for antigens or antibodies that are characteristic of a pathogen are particularly susceptible to problems caused by endogenous binding partners. If the patient being assayed has developed an immune response to the analyte antigen, a significant portion of sample antigen may be present in undetectable endogenous antigen/antibody complexes. Similarly, in serology assays where the antibody is the analyte to be measured, some of the sample antibody that the assay is designed to measure may be complexed with endogenous pathogen antigen.

In addition to endogenous antibody/antigen complexes, other endogenous complexes can interfere with assays, for example, various serum globulins can interfere with immunoassays for thyroxine, estradiol, cortisol, and testosterone. See, Thorell, J. I., and Larson, S. M, in "Radioimmunoassay and Related Techniques," C. V. Mosby, St. Louis, 1978. Vitamin $B_{12}$ assays are perturbed by the binding of transcobalamin. See, Laue et al. Blood 26:202 (1965). Immunoassays for prostate-specific antigen (PSA) are perturbed by endogenous complexes with a serine protease inhibitor, $\alpha_1$-antichymotrypsin. See, Lilja et al. Clin. Chem. 37:1618–1625 (1991).

Another area in which endogenous complexes may seriously affect assay results is the use of tumor antigens to mark the tumor's presence, e.g. in an immunoassay. Frequently, these tumor markers may be masked by endogenous complexes. For example, serum thyroglobulin autoantibody interferes with detection of differentiated thyroid carcinoma. Another example of the difficulty of obtaining accurate quantitation of a serum tumor antigen is the epithelial mucin MUC-1. Gorevitch et al., Br. J. Cancer, 72:934–938 (1995); and Hilgers et al. Scand. J. Clin. Ob. Invest. Suppl., 221:81–86 (1995).

A particular problem which may be related to endogenous complex formation has surfaced in HIV assays. Tsiquaye et al., AIDS, 2:41–45 (1988); McHugh et al., J. Infect. Dis., 158:1088–1091 (1988); Nishanian et al., J. Infect. Dis., 162:21–28 (1988); and Carini et al., Scand. J. Immuno., 26:1 (1987). Other assays in which this problem can arise include: epithelial mucin (MUC-1 and PEM) assays (Gorevitch et al., Br. J. Cancer, 72:934–938 (1995); and Hilgers et al. Scand. J. Clin. Ob. Invest. Suppl., 221:81–86, 1995); Hi histones in assays for systemic lupus (Wesierska-Gadek et al. Arthritis Rheum, 33:1273–1278, 1990); assays for the tuberculosis pathogen (Dlugovitzky et al. Braz. J. Med. Biol. Res. 28:331–335, 1995); alpha-fetoprotein assays to detect hepatocellular carcinoma (Tsai et al., Br. J. Cancer, 72:442–446, 1995); assays for Yersinia enterocolitca and Yersinia pseudotuberculosis (Didenko et al. J. Basic Microbiol. 35:163–170, 1995); and assays for the leprosy pathogen (Sinha et al. Int. J. Lepr. Other Mycobact. Dis., 60:396–403, 1992).

Various methods have been described to dissociate endogenous antibody/antigen complexes and thereby to improve assay sensitivity, including solvent extraction, heating, protein precipitation, use of competitive inhibitors, and pH changes. For example, Mosier, U.S. Pat. No. 4,656,251, and Weil et al., J. Immunology, 134:1185–1191 (1985), disclose pretreating a canine sample to break up immune complexes before assaying for heartworm antigens. Mosier '251 discloses a process that includes acidification to dissociate the complex, followed by heating to denature dissociated antibodies. Weil discloses (p. 1186, right column) a process including the addition of EDTA followed by heating.

Accelerating High Sensitivity Assays: While sensitivity may be improved by lengthening incubation time (e.g., overnight), high throughput and automation are also important goals that may be inconsistent with lengthy incubation. As high throughput automated instruments have become widely utilized, assay results are needed more quickly (i.e., within a few minutes). The need to accelerate analyte/binding partner interactions may be addressed by adding a large excess of the exogenous binding partner, or by using temperature conditions above optimum to drive the binding reaction as far as possible in an acceptable assay time.

Separation of Biomolecules: A widely accepted method for purification of bioactive compounds is affinity chromatography. This method is based on the premise that many bioactive compounds bind to other molecules with extraordinary specificity. These other molecules are commonly referred to as "ligands." For example, ligands that-have been identified for binding specific compounds include, but are not limited to, nucleic acids, vitamins, carbohydrates, fats, and proteins (e.g., enzymes, antibodies, and receptors).

The first step in affinity chromatography typically is identification of a ligand that binds specifically to the compound of interest. Such ligands are already known for many enzymes and other compounds. Once a ligand has been identified and obtained, the ligand can be attached to a solid support. The solid support can, for example, be trapped within a porous sack or, more commonly, immobilized in a porous column. A solution known to contain, inter alia, the compound of interest is generally flushed through the column so that the solution comes into binding contact with the immobilized ligand.

The quantity of immobilized ligand required depends on the amount of the desired compound expected to be present. Typically, each ligand can bind to a limited number of (e.g., often one) molecules of the compound. Numerous complications render this generalization less valid in practice, however. For example, steric constraints can limit the number of molecules of the compound that can exist within a given volume, especially if the compound is, for example, a relatively large molecular weight, multi-domain protein. Also, there can be other, undesirable compounds capable of weakly binding to the same ligand that the compound of interest binds tightly to. The latter problem can become especially acute if the undesired weakly binding compound is present in excess (i.e., relative to the desired compound). Therefore, it is desirable to promote high affinity, high specificity interactions.

In a typical preparative application of affinity chromatography, an impure solution containing the desired compound is passed through a porous material (e.g., in a bed or column) containing the immobilized ligand. The desired compound becomes bound to the ligand and therefore is itself immobilized. The remaining impurities that were in the solution, including other compounds, are washed away with an additional fresh buffer or solvent, leaving the immobilized ligand bound to the desired compound.

Once the impurities have been washed away, the compound of interest can be released from the binding relationship with the immobilized ligand. This process is called "elution." Elution can be effected by making the compound-ligand complex unstable, for example, with altered pH, temperature, or ion concentration, or by adding a different ligand known to have still greater affinity for the compound relative to the immobilized ligand (i.e., to displace the compound). It is desirable to effect elution with relatively mild conditions to avoid irreversible damage to either the ligand or the desired compound. It is also desirable to elute the desired compounds under conditions that ensure simple recovery following separation.

Affinity chromatography sometimes uses antibodies, enzymes, or other binding proteins as the immobilized member of the binding pair, with the specific ligand or substrate being the desired compound to be isolated or purified. The type of affinity chromatography termed immunoaffinity chromatography uses antibodies as ligands. Some advantages of immunoaffinity chromatography are that: 1) the immunological process of antibody diversity does the work of finding a ligand, and 2) antibodies exhibit high specificity.

SUMMARY OF THE INVENTION

The invention features: (1) pressure-mediated dissociation of an analyte complexed with an endogenous binding partner to enable detection of a complex formed from the analyte and an exogenous binding factor, (2) pressure-mediated association of an analyte and an exogenous binding partner to enable more rapid and/or more sensitive detection of an analyte, and (3) pressure-mediated association and dissociation of biomolecular complexes to enable separation of one biomolecule from a complex mixture.

Pressure can be used to improve assays by dissociating endogenous analyte complexes and improving assay speed and sensitivity by associating the analyte molecules with exogenously supplied binding partners. Pressure can also be used to improve the separation of compounds from contaminated mixtures.

Assays: Pressure can be controlled to dissociate endogenous analyte complexes and thereby improve detection of analyte present in samples containing endogenous components that complex with the analyte. As described above, such endogenous complexes can interfere with analyte detection in various ways. One specific example of such interference involves detection formats that rely on a determination of complexing between analyte and an exogenously supplied specific binding partner for the analyte.

In one aspect of the invention, endogenous analyte complexes are dissociated under controlled pressure to improve analyte availability for detection. For example, pressure-induced dissociation of the endogenous complexes (weak or strong) can improve analyte detection by improving binding (i.e., kinetically or thermodynamically) to the exogenous binding partner. This aspect of the invention features a dissociation step in which the sample is subjected to elevated pressure sufficient to dissociate an endogenous complex formed from an analyte and an endogenous sample component (e.g., preferably at least 15,000 psi, i.e., 105 MPa, and most preferably at least 30,000 psi, or 210 MPa). This dissociation step is followed by an analyte detection step, e.g., in which the exogenous specific binding partner is reacted with sample analyte. In this format of the invention, it is believed that increasing the pressure results in structure disruption (either a reversible or irreversible change in three-dimensional conformation) of a component of the endogenous complex which prompts binding partner dissociation.

More specifically, the dissociation pressure can (but need not necessarily) be high enough to irreversibly dissociate the analyte from endogenous binding component. If dissociation is irreversible (for example, because one member of the complex is structurally disrupted in a way that substantially prevents endogenous complex reassociation), then the assay step can be performed without first removing the structurally disrupted binding component from the analyte. If desired, an agent that prevents or reduces reassociation can be added, such as a denaturing agent (e.g., urea); a water miscible solvent; a chelating agent, such as EDTA, EGTA, or o-phenanthroline; a detergent; or a chaotrope, such as dithiothreitol, urea, or thiocyanate. This agent or agents preferably should be tolerated in subsequent assay steps, so that it need not be removed prior to those steps.

For reversible dissociation, the analyte is removed from the endogenous sample component in a separate step performed after the dissociation step. For example, the exogenous analyte binding reagent can be immobilized in a chamber with the sample; chamber pressure is increased to dissociate the complex, after which the endogenous binding component is removed from the chamber while pressure is maintained. The chamber can be a semipermeable membrane selected to pass endogenous analyte, but not endogenous sample component.

In another embodiment (or in a combination of the above described embodiments), temperature, pressure, or both, are controlled (usually increased) to control the association between a ligand present in a mixture and an exogenously supplied binding partner. For example, an assay is performed where pressure and temperature are maintained to improve association compared to ambient (1 atm, room temperature) conditions. It is possible to combine the various aspects of the invention by first subjecting a mixture to a temperature and pressure for separating a ligand (analyte) in the mixture from endogenous binding partners in the mixture, and then changing temperature or pressure, or both, of the separated ligand to a second temperature or pressure, or both, selected to enhance ligand complex formation relative to complex formation at ambient temperature and pressure. Generally, the second temperature or pressure is intermediate between ambient conditions and the temperature and pressure used in the separating step above. While at the second temperature and pressure, the separated ligand is reacted with the exogenously supplied binding partner.

The method can be performed using apparatus (described in PCT/US96/03232, incorporated by reference) in which a valved inlet connects the chamber to a pressurized supply area, a valved outlet connects the chamber to a waste collection area, and controllers operate the valved outlets. Analyte is flushed out of the chamber and into the collecting chamber by introducing material from the pressurized supply area.

The invention can be practiced with a wide diversity of analytes. In particular, the analyte may be an antigen, and the method may be used to dissociate an endogenous antibody that complexes with the antigen. Where the analyte is an antibody, the method can be used to dissociate a complex between an antigen and the antibody. In addition, where the analyte is complexed with multiple endogenous components, the method can be used to dissociate the analyte from such one or more of these complexes.

Such dissociation is particularly useful where endogenous complexes are known to interfere at least to some extent with assaying. The invention can specifically be used to assay: a) HIV antigens (e.g., p24, gp41, gp120, gp160, and p15) where the sample is a human bodily fluid containing anti-analyte antibody; b) non-protein analytes, such as thyroxine, estradiol, cortisol, and testosterone, where the sample is a bodily fluid comprising serum globulin; c) Vitamin $B_{12}$ where the sample contains transcobalamin; d) prostate-specific antigen where the sample contains α1-antichymotrypsin or α2-macroglobulin; e) an epithelial mucin, where the sample contains endogenous antibody that complexes with the analyte; f) antibody to Hi histones in an assay for systemic lupus, where the sample contains endogenous H1 histones; g) tuberculosis pathogen, where the sample contains anti-analyte antibodies; h) alpha-fetoprotein where the method is a diagnostic for hepatocellular carcinoma; i) an antigen of *Yersinia enterocolitca* or *Yersinia pseudotuberculosis*; j) an antigen of the leprosy pathogen, *Mycobacterium leprae*; k) anti-DNA antibodies or DNA binding thereto; l) *Dirofilaria immitis* antigen or antibody thereto; m) growth hormone or growth hormone-binding protein; n) cholesterol; o) low density lipoprotein; p) high density lipoprotein; and q) tumor antigens that can be used as diagnostic, monitoring, or prognostic indicators for cancer-related pathological states.

A specific concern with many tumor markers is that although they are often detected in benign disease, they may be absent in early-stage malignancy, due to complex formation with a patient's antibodies. For example, serum thyroglobulin autoantibody interferes with detection of differentiated thyroid carcinoma. With proper controls and dissociation of complexes, tumor markers may be used to quantitate tumor burden, e.g., to monitor clinical progress and patient status. In particular, tumor antigen burden can be measured serially over time. The invention also permits separation of total analyte levels into dissociated analyte and analyte present in endogenous complexes. The information thus derived, e.g., autoantibody levels, can be useful clinically. Where free antigen and complexed antigen appear out of balance, the balance can be corrected extracorporeally to increase both cellular and humoral cytotoxicity to the tumor.

Not only does the invention improve assays involving endogenous complexes, it also makes possible a better understanding of precisely how much and what type of antigens and antibodies are present, regardless of whether they are present in complexes. This capability can improve the ability to track the immune response to, and the course of, a disease.

The invention may also improve assays in which the endogenous analyte is not initially complexed with the analyte, but the assay protocol and reagents induce formation of such an undesired complex. The term "endogenous complex" includes such undesired complexes which are induced by the assay, even complexes which form with assay components; so long as the complexes are not the desired complex which results in a detectable event. Pressure control can also ameliorate such de novo assay-induced complex formation.

The invention also includes an embodiment wherein the dissociation of endogenous binding complexes is accompanied by association of an exogenous binding partner such as an aptamer.

Separation: Pressure's influence on affinity can be used to improve affinity chromatography methods. Contaminated mixtures containing compounds of interest can be placed in fluid contact with molecules known to bind to the desired compounds with pressure-dependent affinity or activity. The pressure in the reaction vessel can be altered to allow the desired compounds to bind more quickly or more tightly to the immobilized molecules. The contaminants can be flushed away first, and then the purified compounds can be dissociated from the immobilized molecules, for example by further modifying the pressure.

In general, the invention features a method for separating a desired compound from at least some contaminants in a mixture containing the desired compound and one or more contaminants. The method includes providing binding molecules having pressure-dependent affinity for the desired compound, providing the mixture (i.e., in fluid contact with the binding molecules), and subjecting the molecules and the mixture to a first pressure that increases the affinity of the binding molecules for the desired compound, to form a bound complex. These steps can be performed in any order. The bound complex is then separated from at least some of the contaminants, the pressure is changed to a second pressure (i.e., which decreases the affinity of the binding molecules for the desired compound), and the binding molecules are finally separated from the desired compound.

In the present context, the term "affinity" is used to describe both the kinetics and thermodynamics of binding. Thus, when it is said that a set of conditions "enhances the affinity of an analyte for a reagent," it is to be understood either that the conditions enhance the rate of formation of an analyte-reagent complex or that the conditions drive the equilibrium of the reaction system toward complex formation, or both. "Enhanced ligand complex formation" would have the same meaning.

Furthermore, the phrase "molecules that associate with a compound in a pressure-dependent manner" means that either the rate of the association (i.e., binding molecule-desired compound complex formation) is increased or the equilibrium of the system is shifted toward association, or both.

The first and second pressures can each be uniform throughout the system that includes both the binding molecules and the mixture in fluid contact with the molecules.

The binding molecules can be immobilized, for example by attachment to a solid support (e.g., a polymer bead, a particle, a strip, a tube, a column, a molded material, and a polymer matrix) or by using a semipermeable membrane that passes only one of the components of the binding pair.

The fluid mixture can include, for example, water, an aqueous solution, an organic solvent, an organic solution, a gas, or a supercritical fluid.

The desired compound and the binding molecules can include, but are not limited to, members of the following classes which can form bound complexes: polypeptides, proteins, antigens, haptens, antibodies, prions, carbohydrates, nucleic acids, steroids, triglycerides, substrates, enzymes, and hormones. Thus, the bound complex can be, for example, an enzyme-substrate complex, a ligand-receptor complex, a glycoprotein-lectin complex, a protein-cofactor complex, a nucleic acid-cofactor complex, a hybridized nucleic acid-target complex, a hapten-antibody complex, or an antigen-antibody complex.

The first pressure, or both the first and second pressures, can be greater than atmospheric pressure (e.g., between 500 and 200,000 psi or between 5,000 and 200,000 psi).

The first pressure can be applied prior to or after providing the mixture, the binding molecules, or both.

pH, ionic concentration, fluid composition, or temperature can be modified to enhance separation of the compounds of interest from the binding molecules. Additionally, a reagent can be added to cause dissociation of the bound complex to yield the free compound of interest and the unbound molecules. The reagent can be, for example an acid, a base, a salt, a metal, a metal-scavenger, a detergent, a dissociating agent, a chaotropic agent, water, an organic solvent, a chelating agent, or some other binding partner. More specifically, such a reagent can be, for example, a magnesium salt, a lithium salt, sodium dodecyl sulfate, urea, guanidine hydrochloride, thiocyanate, or dioxane.

The desired compound can be, for example, an enzyme (wherein the binding molecules can be substrates for the enzyme); an antibody, such as a monoclonal antibody (wherein the binding molecules can be antigens for the antibody); or a cofactor, such as a transcription cofactor (wherein DNA transcription can be modulated).

The three-dimensional conformation of the desired compound can, for example, change in the transition from the first to the second pressure.

In another embodiment, the invention features another method for separating a compound of interest from at least some contaminants in a mixture containing the desired compound and one or more contaminants.

This method includes providing binding molecules having affinity for the desired compound and further having pressure-dependent activity for the modification of the desired compound. This means that the binding molecules not only bind to the desired compound, but also cause a modification of the compound. An example of such a system is provided by an enzyme and its substrate. At atmospheric pressure, many enzymes bind to their substrates, modify the substrates to generate "products," then release the products.

The modifying activity of many such enzymes is attenuated by elevated pressure, while binding affinity is often enhanced by pressure. Thus, the enzyme's ability to bind to the substrate can be exploited for purification, provided that the pressure is not lowered to a level at which the enzyme exhibits modifying activity.

The method of this embodiment also includes providing the aforementioned mixture in fluid contact with the binding molecules to form a bound complex at a first pressure that decreases the activity of the binding molecules for the modification of the compound. These two steps can be executed in any order. The bound complex is then separated from at least some of the contaminants.

In some examples, the pressure is changed to a second pressure (i.e., that increases the activity of the binding molecules for the modification of the compound) and the unbound molecules are finally separated from the modified compound (i.e., the product).

Alternatively, or additionally, pH, ionic strength, fluid composition, or temperature can be modified to enhance separation of the compounds of interest from the unbound molecule.

In another alternative method, a reagent that causes dissociation of the bound complex is provided, and the binding molecules are separated from the desired compound. Examples of such reagents include acids, bases, salts, metals, metal-scavengers, detergents, dissociating agents, chaotropic agents, water, organic solvents, chelating agents, and other binding partners. Specifically, the reagent can be, for example, a magnesium salt, a lithium salt, sodium dodecyl sulfate, urea, guanidine hydrochloride, thiocyanate, or dioxane.

The first pressure can be uniform throughout the system that includes the binding molecules and the mixture in fluid contact with each other.

The binding molecules can be immobilized, for example, by compartmentalization within a semipermeable membrane or by attachment of the binding molecules to a solid support (e.g., a polymer bead, a particle, a strip, a tube, a column, a molded material, or a polymer matrix).

The fluid mixture can be, for example, water, an aqueous solution, an organic solvent, an organic solution, a gas, or a supercritical fluid.

The desired compound can be, for example, a polypeptide, a nucleic acid molecule, an antibody, a triglyceride, a steroid, a prion, or a carbohydrate.

The binding molecules can be, for example, enzymes, wherein the bound complex can be an enzyme-substrate complex.

Alternatively, the desired compound can be, for example, an enzyme, wherein the binding molecules can be substrates for the enzyme.

The first pressure can be greater than atmospheric pressure (e.g., between 500 and 200,000 psi or between 5,000 psi and 200,000 psi). The first pressure can be applied prior to providing the mixture. The second pressure can also be greater than atmospheric pressure.

In any embodiment, the method can be repeated at least once (e.g., 1, 2, 3, or more times) to remove more of the contaminants from the mixture.

Screening: In another embodiment, the invention features a method of screening a molecular library for molecules that bind a target. The method includes the steps of providing a member of the molecular library in fluid contact with the target at atmospheric pressure to form a complex; using a detection means to monitor the binding rate and affinity in real-time; subjecting the complex to an elevated pressure that causes dissociation of the complex; flushing the dissociated member away from the immobilized target; repeating these steps for other members of the library; and then analyzing the results collected by the detection means to determine which members of the library bind to the target.

The library can, for example, include proteins, carbohydrates, antibodies, ribozymes, oligonucleotides, peptides, or small organic molecules. The target can be, for instance, a phage display or other immobilized biomolecules. The detector means can be, for example, a radioisotopic detector, an infrared spectrometer, a mass spectrometer, a gas chromatograph, a spectrophotometer, a spectrafluorometer, an electrochemical detector, a surface plasmon resonance detector, a nuclear magnetic resonance spectrometer, a scanning tunneling microscope, an atomic force microscope, or a chemiluminescence spectrometer.

Refolding of Denatured Proteins: In still another embodiment, the invention features a method of refolding a previously denatured protein. The method includes the steps of subjecting aggregates of the denatured protein to elevated pressures sufficient to break up the aggregates to form dissolved, denatured polypeptide chains and then rapidly cycling the pressure to cause the dissolved, denatured polypeptide chains to rapidly sample numerous conformations until the polypeptide chain has folded into its lowest energy protein conformation.

In certain cases, the aggregates are mixed with a pressure-sensitive buffer and contacted with a solid phase having an ionization volume of opposite charge to that of the buffer. The pressure cycling is thought to disrupt the aggregates by pH fluctuation and disperse the aggregates by reversible binding to the solid phase. The buffer itself can be covalently bonded to a solid support (which may or may not be the same as the solid phase), and can also serve as a nucleation site for the refolding of the polypeptide chain. In some cases, reducing and oxidizing agents can be added to allow reconfiguration of disulfide bonds within the polypeptide chain.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

An advantage of the claimed invention is clean separation and isolation of the purified compounds. In certain embodiments, the desired compounds can be eluted from the immobilized binding molecules without addition of supplementary reagents. No packing matrix is necessary either, which means that less of the desired compound is lost through non-specific adsorption as is common in the elution or fractionation steps of traditional chromatographic methods. A packing matrix is a material which can be packed inside a column either to provide a solid phase for the immobilized "capture" reagent or to effect separation by another route such as size exclusion chromatography. The moderate pressures used successfully in the present methods are less likely than the traditional methods to cause irreversible damage either to the desired compounds or to the immobilized binding molecules. Other features and advantages of the invention will be apparent from the following detailed description, and from the claims.

DETAILED DESCRIPTION OF THE INVENTION

Figure 1:
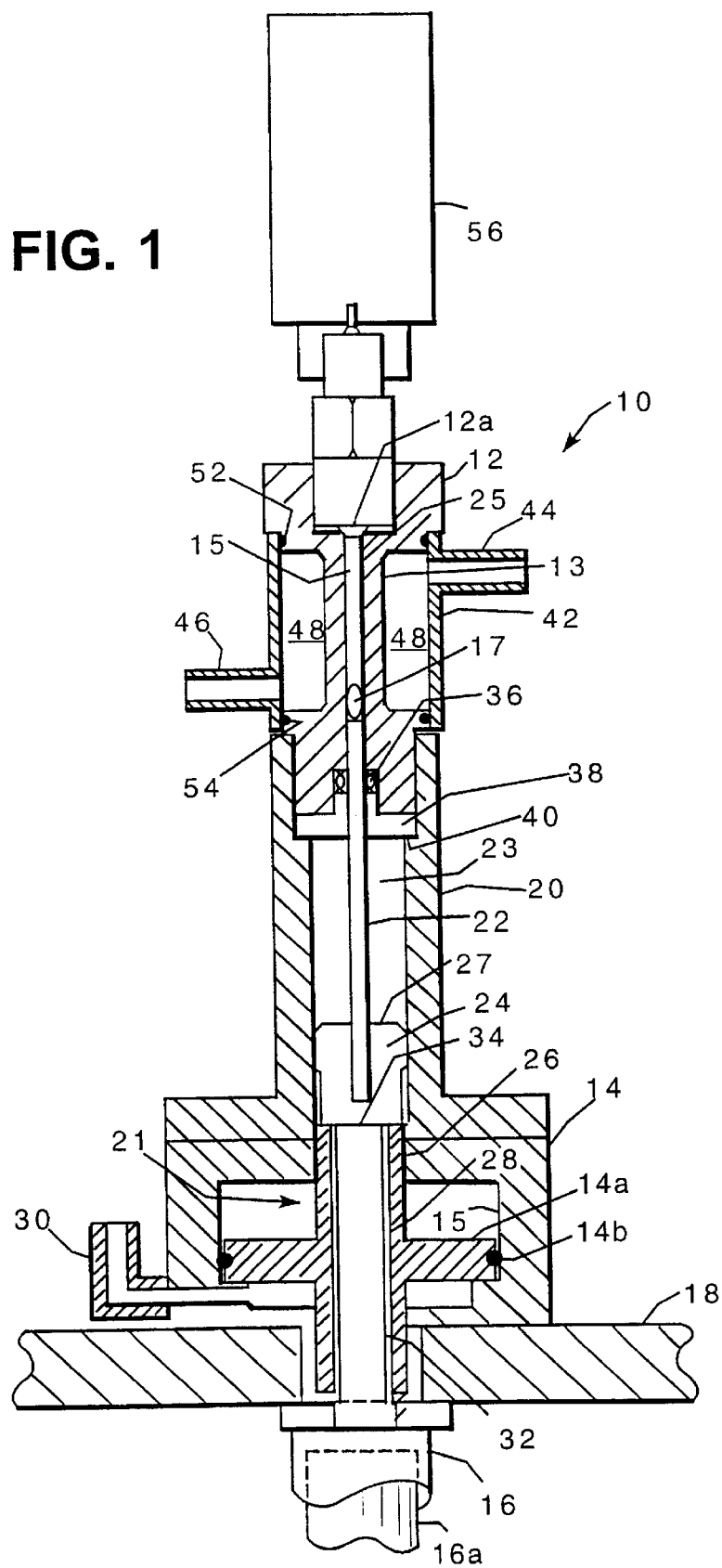
FIG. 1 is a schematic of a reactor that can be used to apply pressure to assay reagents.

Assays: Various detailed embodiments are discussed in greater detail below. As noted, some of these embodiments involve either irreversible or reversible separation of endogenous complexes. Other embodiments improve association of the desired (exogenous) complex. General considerations regarding pressure selection to achieve these various embodiments are also discussed below.

Irreversible dissociation: Generally, irreversible separation requires sufficient pressure to irreversibly alter at least one complexing member, e.g., by irreversible structure disruption (e.g., alteration of the tertiary structure) of a protein. It is usually preferable to disrupt the structure of the endogenous sample component, rather than the analyte, so as not to affect analyte binding to the exogenous binding partner. In some cases, however, it may be possible to irreversibly alter the analyte so as to prevent reassociation of particularly troublesome endogenous complexes, without affecting the analyte binding characteristics necessary for the assay. Typically, where the analyte is a non-protein antigen, and the endogenous complex includes an endogenous antibody, the pressure can be used to irreversibly disrupt the structure of the endogenous antibody without substantially affecting the antigen. In the case of serological assays, the endogenous antibody is the analyte and it would be preferable to irreversibly disrupt the structure of the antigen resulting from the host infection.

Pressures over 60,000 psi have been shown to effect irreversible separation of endogenous complexes, such as immunocomplexes. Pressure generally will not be high enough (e.g., not over 150,000 psi, and preferably not over 80,000 psi) to irreversibly alter the analyte.

In one format of irreversible structure disruption, the sample is loaded in a small pressure vessel, such as is disclosed in commonly owned PCT/US96/03232, filed Mar. 7, 1996, entitled "Pressure Cycling Reactor," hereby incorporated by reference. Pressure is increased to between 30,000 and 60,000 psi and then returned to a pressure that permits or even enhances the complex formation necessary for assay determination.

Determination of the optimum pressure may involve identification of the range in which desired irreversible structure disruption occurs without adversely affecting other system components. As described below, analyte binding generally is related to temperature and pressure. First, analyte pressure sensitivity can be determined by simple experiments in which analyte solutions are subjected to increasing pressures (e.g., 1,000 to 60,000 psi) and then assayed with standard techniques to determine a structure disruption threshold for the exogenous complex used in that assay. Then, actual samples containing endogenous complexes can be subjected to pressures below that threshold to determine whether irreversible complex separation occurs.

If necessary, temperature can be modulated to promote structure disruption. For example, at low temperature, pressure-induced structure disruption occurs at lower pressure than at ambient temperature. At high temperature, higher pressure is required to promote structure disruption than at ambient temperature. Further control may be achieved by adding agents such as chaotropes, water miscible organic solvents, chelating agents, detergents (e.g., triton X-100), urea, thiocyanates, acids, bases, etc. Preferably, the concentration of such agents is low enough to neither cause complex separation at ambient pressure nor affect subsequent assay steps. High pressure makes the complex components particularly vulnerable to these agents; thus, low concentrations can be effective.

Once the sample pressure has been reduced (e.g., to ambient pressure), the assay can then be performed according to any of the many well known formats, including competitive and excess reagent immunoassays and affinity labeling formats. Those skilled in the art will appreciate that there are many suitable immunoassay formats, relying on various reagents (e.g., enzymatic reactions that generate color, fluorescent reactions, radiolabels, colloidal gold, and many others) to permit visualization and/or quantitation of analyte.

Those skilled in the art will also understand that there are many suitable physical formats and devices that can be used. For example, the pressure treated sample can simply be removed from the pressure vial and applied to a standard solid phase capture format (see, e.g., David et al., U.S. Pat. Nos. 4,486,530 and 4,376,110).

The reagents used in the above-described formats can also be varied without altering the spirit of the invention. Monoclonal antibody-based technology can be selected for the specific properties at issue, e.g., the ability to bind an epitope of the sample antigen that is insensitive to the pressures used to structurally disrupt other epitopes. Standard monoclonal antibody screening techniques that can be used to obtain such antibodies will be apparent from this description.

Reversible Dissociation: In one embodiment, the pressure dissociates the endogenous antibody sample complexes, followed by separation of the desired fraction to allow detection of the partner. There are a number of ways this can be accomplished. For example, if the aim is to detect antigen that has been complexed by antibody, the addition of (or to) an excess of immobilized antigen will effectively bind up the antibody and remove it from the system. The completeness of this dissociation will depend on the amount of excess reagent.

Other separation techniques include physical fractionation by size (e.g., gel filtration to allow the large molecular weight component to wash through), the use of solvents to extract small hydrophobic antigens, or removal of freed up antibody by affinity extraction using an immobilized secondary antibody.

It will be apparent to those skilled in the art that many physical and immunological separation techniques are potentially applicable as a means to separate or otherwise inhibit the newly uncomplexed component to prevent it from reassociating.

Figure 2:
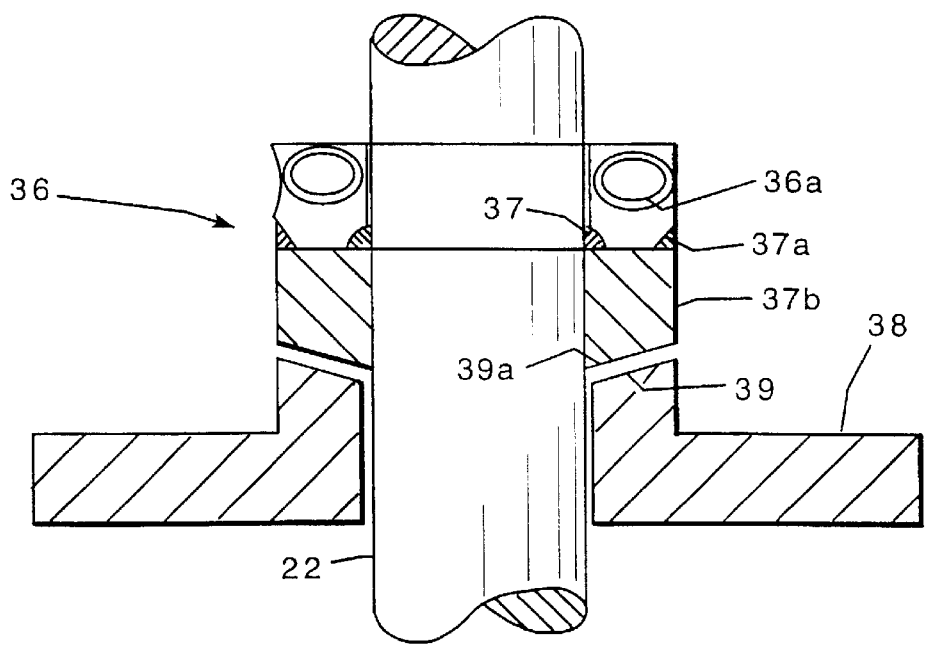
FIG. 2 shows a spring seal and gland washer of the reactor of FIG. 1.
Figure 3:
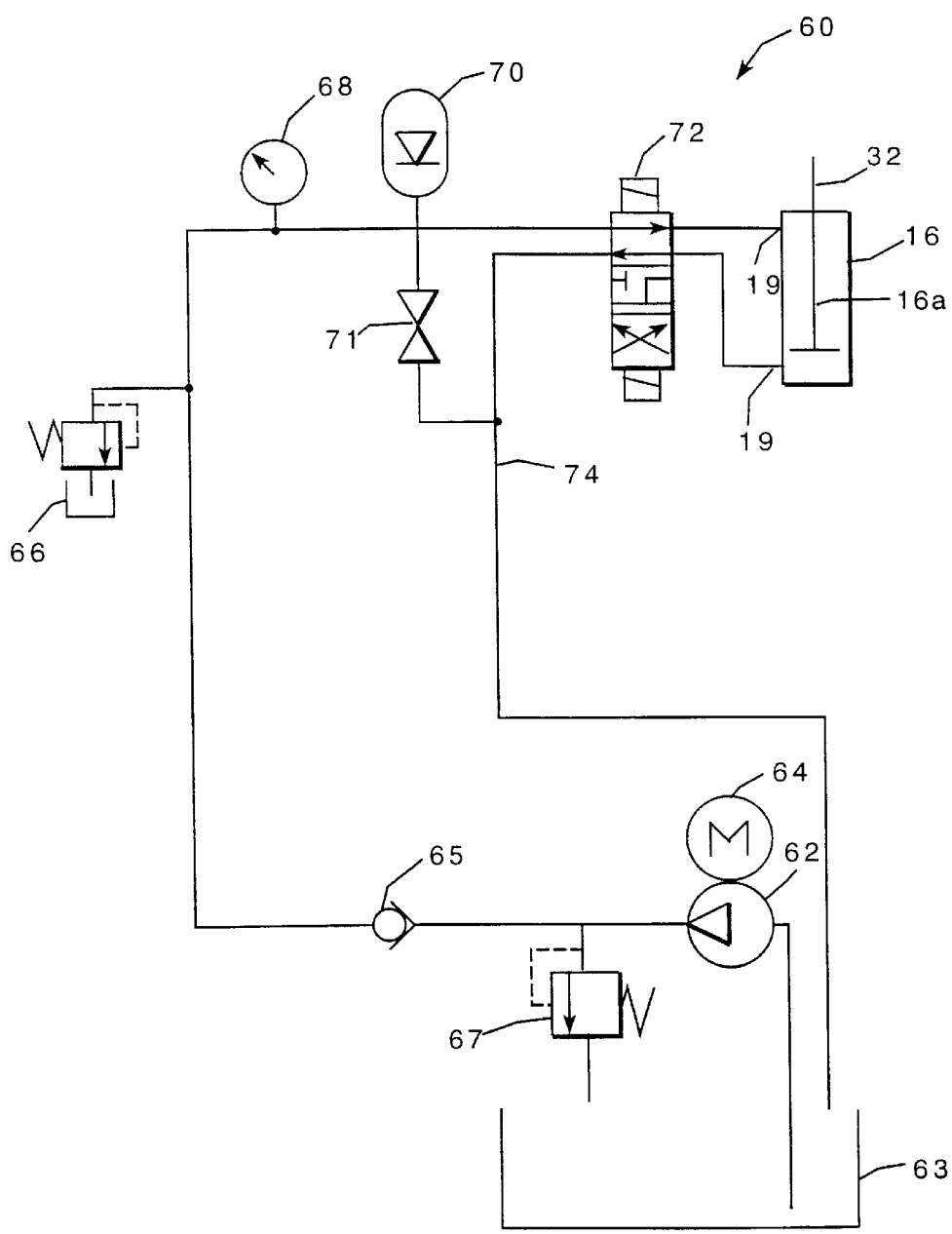
FIG. 3 is a schematic of the hydraulic system of the reactor of FIG. 1.

FIGS. 1–3, abstracted from PCT/US96/03232, incorporated by reference, disclose an apparatus that can be used to maintain high pressure on a sample, as described below. Another apparatus is described therein, that allows reagents to flow through a high-pressure reactor to remove separated endogenous sample components from the chamber.

Pressure cycling Reactor: Referring to FIG. 1, a reactor 10 includes a reaction module 12 having a wall 13 defining a chamber 15 for containing a sample capsule 17, made from, e.g., polyethylene. A port 12a in reaction module 12 permits placement of capsule 17 into chamber 15. A short stroke pressure transmitting pneumatic cylinder 14 and a pressure transmitting hydraulic cylinder 16 for applying pressure to chamber 15 are mounted to a base plate 18. Reaction module 12 is supported by a truss made of, e.g., stainless steel, defining a variable volume pressure chamber 23. A piston 22 having, e.g., a 3/16" diameter, supported and guided by a bearing 24 made from, e.g., a bronze alloy, and defining a chamber wall 27 communicates between a bore 25 in reaction chamber 12 and cylinders 14 and 16. Piston 22 along with cylinders 14 and 16 form a vessel pressurizer 21 which controls the pressure in chamber 15. Reaction module 12 is made from, e.g., stainless steel and bore 25 has a diameter of about 0.188" and a length of about 1".

Referring also to FIG. 2, a seal 36, e.g., a spring energized seal including a spring 36a and back-up washers 37, 37a, and 37b available from Bal Seal Engineering Co. Inc., Santa Ana, Calif., supported by, e.g., a gland washer 38, seals piston 22 within reaction chamber 12. Gland washer 38 includes an inclined surface 39 which mates with an inclined surface 39a of back-up washer 37b. Spring 36a ensures sealing at low pressures and assists sealing at higher pressures. The back-up washers and the gland washer act to prevent extrusion of seal 36 under pressure. Gland washer 38 is supported by a shelf 40 in truss 20.

Pneumatic cylinder 14 includes a piston 14a having, e.g., a 2.5" diameter, with an extension rod 26 having a through bore 28. O-ring 14b forms a seal between piston 14a and an inner wall 15 of pneumatic cylinder 14. When pneumatic cylinder 14 is energized, pressure on piston 14a is transmitted to guide bearing 24 by rod 26 creating an upward force on piston 22. This force is adjustable by varying the pressure to the pneumatic cylinder from a source (not shown) attached to inlet 30. The force applied to piston 22 by pneumatic cylinder 14 determines the low pressure level within reaction chamber 12 during pressure pulsing. Pneumatic cylinder pressure is adjustable up to about 100 psi (which produces a pressure of about 17,000 psi in reaction chamber 12).

Hydraulic cylinder 16 includes a piston 16a having, e.g., a 1" diameter, with an extension rod 32 projecting up through bore 28 of pneumatic cylinder rod 26. The end 34 of hydraulic rod 32 bears against guide bearing 24. On extension, hydraulic rod 32 drives piston 22 upwards. The pressure generated by hydraulic cylinder 16 plus the pressure generated by pneumatic cylinder 14 determines the high pressure level in the reaction chamber. Hydraulic cylinder pressure is adjustable with an upper limit set at approximately 1,500 psi. The ratio of the cross-sectional area of hydraulic piston 16a to the cross-sectional area of piston 22 is 28.4:1.

Reaction module 12 is surrounded by a thermostatting jacket 42 to control the temperature of the reaction chamber. Jacket 42 has inlet and outlet fittings 44, 46, respectively, which permit fluid to be circulated into chamber 48 surrounding wall 13 from a temperature controlled heating/ refrigeration bath (not shown). Around the top and bottom of reaction chamber 12 are O-rings 52, 54 which provide a fluid seal for thermostatting jacket 42. A thermocouple (not shown) is mounted to reaction chamber 12 to monitor the temperature of the chamber. The temperature of chamber 12 is controlled within a range of about −15° C. to +40° C. with an accuracy of about +/−1° C. The thickness, e.g., 3/16", of wall 13 is selected to be thin enough to permit heat transfer from thermostatting chamber 48 to sample chamber 15 while being thick enough to withstand the pressures applied to sample chamber 15. The maximum allowable pressure in reaction module 12 as determined by the thickness of wall 13 as well as by the performance of seal 36 is about 40,000 psi.

Mounted at the top of the assembly is a pressure transducer 56, for example, a 75,000 psi, +/−0.5% accuracy strain gauge type transducer available as part number HP/5651-02-02 from Sensotec, Inc., Columbus, Ohio. Pressure transducer 56 is removed from reaction module 12 to allow access to port 12a.

Referring to FIG. 3, hydraulic pressure is delivered to hydraulic cylinder 16 by an hydraulic pump 62. An hydraulic system 60 includes hydraulic pump 62 driven by a motor 64, a fluid reservoir 63, a relief valve 67, a check valve 65, a pressure adjustment valve 66, a pressure gauge 68, an accumulator 70, a manual valve 71, a four-way directional control valve 72, and hydraulic cylinder 16.

Motor 64 is, e.g., a 2 HP electric motor with an output of 0.8 GPM at 3,000 psi max. Actual system pressure is controlled by pressure adjustment valve 66 and is variable up to the set upper limit of approximately 1,500 psi.

Directional control valve 72 is, e.g., a three position spring centered spool valve actuated by dual electrical solenoids, available as Bosch part #9810231072 from Pearse-Pearson, Inc., Milford, Mass. With both solenoids de-energized, both hydraulic cylinder ports 19, 19a are connected to a drain line 74, and cylinder piston 16a may be freely moved. In use, energizing one solenoid pressurizes port 19 and with the other solenoid deenergized so that it is open to drain line 74, piston 16a is forced to extend thus pressurizing sample chamber 15. To now pulse the pressure in the sample chamber, both solenoids are deenergized so piston 16a is free to move and the pressure in chamber 15 forces piston 22 down releasing the pressure in the chamber (to the level of pressure applied by pneumatic cylinder 14). Alternatively, energizing the other solenoid pressurizes port 19a and with the other solenoid deenergized so that it is open to drain line 74, piston 16a is forced to retract. The passive release of pressure from chamber 15 is preferable because it provides for a faster hydraulic response time and the continual contact between piston 22 and rod 32 avoids producing impact loads between the piston and the rod. Directional control valve 72 can be rapidly switched at times down to 20–25 ms to apply pressure to hydraulic cylinder 16 and to allow release of pressure from chamber 15.

Hydraulic accumulator 70 is mounted near directional control valve 72 to enhance response and dampen pressure fluctuations. Accumulator 70 has, e.g., a one quart capacity and is charged by pump 62 to hydraulic system line pressure. The presence of check valve 65 causes accumulator 70 to remain charged after pump 62 is turned off. Manual valve 71 is used to discharge the accumulator and depressurize the hydraulic system. Relief valve 67 limits the maximum delivered pressure from pump 62.

It is not intended that the present invention be limited by the nature of the pressure device. A "manual" instrument system capable of generating pressures of 411 MPa is commercially available; the system uses silicone oil as the pressurizing medium, and has a 2 ml reaction vessel (High Pressure Equipment Company, Erie, Pa.). A schematic of this system is shown in FIG. 1.

In some experiments, the high pressure apparatus is a device having the following components: 1 pressure generator (max. pressure 60,000 psi) cat #37-5.75-60; 1 pressure gauge cat #6PG75; 2 valves cat #60-11HF4; 2 tees cat #60-23HF4; 4, ¼"×6" nipples cat #60-8M4-2; 2, ¼"×2 ¾" nipples cat #60-8M4-1 and 1, 2 ml reaction chamber. A pressure gauge with 5 MPa increments is also connected to the system.

The solutions to be pressurized are placed in small deformable polyethylene capsules that are crimp sealed at the ends. A capsule containing 10 to 50 µl of the enzyme/substrate solution is placed in the reaction vessel, which is then connected to the system and pressurized.

It is contemplated that pressure control can be combined with the use of temperature control. This is useful for, among other things, controlling the enzyme during dead time (e.g., time to mix and load the sample before pressure treatment, and time to unload and remove sample for analysis). In some experiments, separate enzyme and substrate solutions are held on ice. The reaction chamber can be held in a refrigerator (about 5° C.).

Temperature can be used in conjunction with pressure to control enzyme activity, as well. For example, a relatively small decrease in temperature (i.e., 5° C.) can cause significant decreases in the rate of digestion in some enzyme systems, thus providing a researcher with greater control over enzyme activity; this may be especially important during dead time, when it may be advantageous to prevent (to the extent possible without harming the enzyme) the digestion taking place while not under pressure.

Improved association of the desired complex: As noted, pressure control may enhance analyte binding to the selected exogenous binding partner, thereby having a significant effect on assay speed as well as improving affinity, sensitivity, or specificity. Specifically, a pressure regime is selected that improves binding by the pressure selection technique discussed below. Temperature and other assay conditions can be varied to further optimize complex formation for a given assay. These conditions are achieved in a pressure chamber, such as the one discussed above.

Pressure selection: In general, binding partners across a range of pressure sensitivities will have a phase diagram exhibiting both reversible and irreversible disruption of structure and both can be applied to improve assay procedures. To optimize use of pressure (as well as time, temperature and other controls), it is useful to develop such a phase diagram (temperature/pressure/association) for the complex being detected and for any endogenous complexes that may interfere with detection. As noted above, pressure can affect not only the equilibrium of the complex, but also the rate at which that equilibrium is reached. To provide the phase diagram and screen candidate binding partners, one can:

1. define the association rate of the binding partners under ambient conditions (atmospheric pressure and constant room temperature);
2. increase pressure to levels below those which disrupt the structure of the native state of one or both of the complex binding partners, thereby defining the effect of pressure on binding rate and equilibrium;
3. increase pressure level still further to define minimal and maximal pressure for reversible disruption of the structure of one or both of the binding partners; and 4. increase pressure still further to define minimal pressure for irreversible disruption of the structure of one or both of the binding partners. Typically, temperature is kept constant (5–40° C.; with thermostable reagents, the temperature can be increased up to about 95° C.) and a constant pressure pulse, ranging from about 25 milliseconds to about 15 minutes, is delivered.

Incrementally increasing pressure from atmospheric up to 150,000 psi defines four domains:

1. a domain at atmospheric pressure;
2. a domain of enhanced rate of association (typically below 60,000 psi);
3. a domain of reversible dissociation (reversible structure disruption of one or both binding partners), typically between about 30,000 and 100,000 psi; and
4. a domain of irreversible structure disruption of one or both of the binding partners (typically between 100,000 and 150,000).

The steps required to ascertain the pressure boundaries of these domains for a given binding pair include: a) definition of a baseline by determination of the association properties of the binding system at atmospheric pressure and room temperature; b) determination of the association rate in the domain of enhanced association; c) determination of the range of reversible structure disruption; and d) determination of the irreversible disassociation range. Protocols for developing such phase diagrams are provided below.

Figure 4:
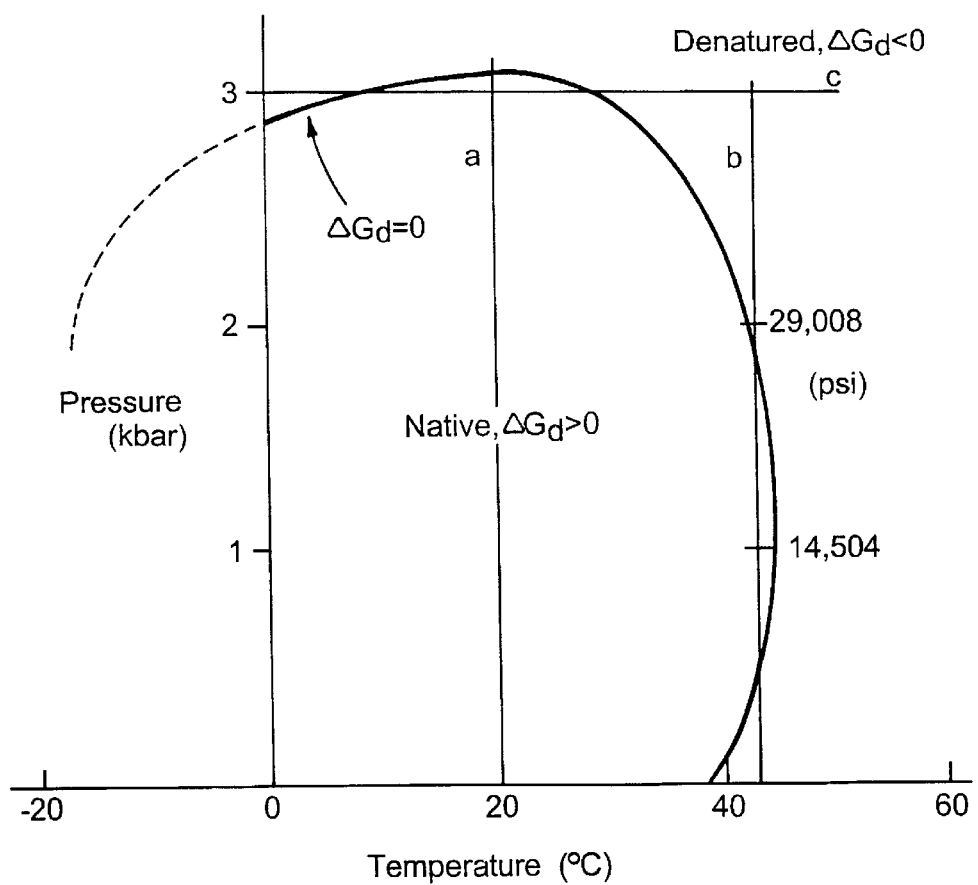
FIG. 4 is a phase diagram.

FIG. 4 shows a typical phase diagram (see Mozhaev et al., TIBTECH 12:496, 1994). Based on such diagrams, it is a routine procedure to determine regions of dissociation and association. The former (dissociation) can be further divided into reversible and irreversible. Once the phase diagram is known, assay pressure may be used to select a desired regime (reversible dissociation, irreversible dissociation, improved association) for operation of the assay.

As a general rule, moderately high pressures (i.e., up to a point) can accelerate the endogenous complex formation. The above-described phase diagram can provide guidance with respect to precise phase boundaries (changes from association to dissociation) for a specific system. While the exact phase boundaries of individual systems may vary, in general, with pH, pressures above 60,000 psi generally will dissociate complexes in standard buffers. At lower pressures, the complex will remain associated, in many cases with either faster kinetics or stronger binding at atmospheric pressure, or both. Without limiting ourselves to a specific molecular mechanism, it appears that differential sensitivity of analytes, such as proteins, to hyperbaric pressure may be related to different primary, secondary, tertiary, and quaternary structures, for example, subunit interactions of oligomeric proteins. Generally, a protein in solution can be introduced into a pressure/temperature reaction chamber. As the pressure is elevated, the protein initially is able to withstand elevated temperature without significant structural disruption. However, as the pressure increases, the solution eventually reaches a transition point beyond which increasing pressure begins to considerably disrupt the structure of the protein from its native state.

The phase diagram also indicates, in general, that although proteins at slightly elevated temperatures can be structurally disrupted, the proteins can generally withstand somewhat higher temperatures without altering their native states if pressure is applied while temperature is kept relatively constant. If, however, the temperature is maintained at a level around 0° C., increasing pressure may disrupt the structure of the protein earlier (i.e., at a lower pressure) than would increasing pressure at ambient temperature; at high temperatures (e.g., 37° C.) the structure is disrupted at still higher pressure. Typically, a protein (analyte) is capable of transitioning reversibly through native and structurally disrupted phases at pressure levels less than 60,000 psi and at temperatures between about 10° C. and about 40° C.

The protein (analyte) can be denatured by any of temperature, pH, or pressure acting independently or in combination. Binder/ligand interactions can be, although are not limited to, a result of one or more of several different types of interactions, such as electrostatic, hydrophobic, aromatic ring stacking, hydrogen bonding, etc. (e.g., van der Waals interactions). These various interactions can interfere with one another constructively or destructively. For example, electrostatic interactions can be both increased (e.g., hydration of a charged group) and decreased (e.g., formation of electrostatic bond) by raising the pressure of a biosystem.

As the pressure of a solution of binding partners is increased, the binder/ligand complexation interactions initially are enhanced. However, as the pressure is increased further, denaturation of the native bimolecular state occurs, prompting dissociation of the binder/ligand complexes. This dissociation may be reversible or irreversible. The dissociation sensitivity is also dependent upon solvents and pH. Improvements in binder/ligand interactions of diagnostic assays are obtained by increasing the pressure of a reaction solution containing the binding partners. As described above, improvement is obtained by two effects, namely: 1) acceleration of binder/ligand interactions; and 2) reduction or elimination of endogenous complex interactions.

Two additional approaches can be used to enhance assays by separating endogenous complexes. The separation can be effectively irreversible, in which case the continued presence of endogenous sample component does not seriously interfere with the assay. Alternatively, the separation can be reversible, in which case the analyte generally should be separated from the endogenous sample component, if possible, to maximize assay sensitivity. Kinetic or thermodynamic advantages may be obtained even without separation, e.g., where the exogenous binding partner must compete with the endogenous sample component to bind analyte.

High Throuqhput Screening: Industrial techniques utilizing molecular diversity enable the randomized generation of large numbers of targets that can, for example, be directed against antibody epitopes. Rapid synthesis of combinatorial libraries that include arrays of novel structures made by the random or directed synthesis of a combination of smaller molecular building blocks requires rapid screening procedures. Molecular diversity can be useful in the discovery of novel proteins, carbohydrates, antibodies, ribozymes, oligonucleotides, peptides, antisense, aptamers, DNA (e.g., single-strand, double-strand, or double-strand with single-strand overhangs), RNA, and small organic molecules. For example, in vitro techniques such as modified recombinant, phage display techniques, which can be used to generate an immune response against a compound of interest, generating as many as $10^5$–$10^8$ antibody sequence variations, or more. Very large combinatorial selection processes can then be performed against the generated antibodies. The binding affinity of the antibody-antigen complex is modulated by the pressure-related processes described herein, enabling faster and more efficient complex selection.

Where it is desirable to monitor the course of the reaction or the products of the reaction, the pressure cycling reactor includes a detector connected to detect a characteristic of a component present in fluid in or removed from the reaction vessel. The detector can be computer controlled and can relay information regarding the analyzed component to the computer. Thus, components can be analyzed before, during, or after a pressure pulse while in the reaction vessel; components can also be analyzed after being removed from the reaction vessel.

Aptamers: One embodiment of the invention features the dissociation of endogenous antibody analyte complexes to facilitate subsequent assay of the released analyte with appropriate immunoassay reagents or immunoaffinity purification. If the pressure phase diagrams of the complexes of the analyte with the endogenous antibody and the immunoassay reagents are sufficiently different, dissociation of endogenous immunocomplexes and association of selected exogenous binding partners can be enhanced simultaneously under suitable pressure conditions. Achievement of this goal requires the identification of specific complexing agents that are useful in immunoassay or affinity purification procedures that, for example, have pressure phase diagrams drastically different from conventional antigen-antibody complexes. A class of reagents that can meet this requirement is the family of oligbnucleotides that bind specific analytes with high affinity. These oligonucleotides are often referred to as aptamers (*Annu. Rev. Biochem.*, 64:763–797, 1995). The interaction of oligonucleotides with ligands such as proteins, polypeptides, and small molecules can occur with very high affinity and great selectivity. Procedures are available for selection of such reagents from random polynucleotide libraries. For example, screening of a randomized oligonucleotide library for binding to basic fibroblast growth factor (bFGF) yielded specific 30-mer sequences that bound to native bFGF with dissociation constants as low as 0.2 nM, while unable to bind to denatured bFGF, an indication of high specificity (*Proc. Natl., Acad. Sci. USA*, 90:11227–11231, 1993). Because the structural principles underlying nucleic acid-ligand interaction and antibody-antigen interaction are fundamentally different (cf. pp.789–790 of Gold et al., *op. cit.*), the probability that the pressure phase diagrams for the binding of a ligand to an aptamer and to an antibody are different is very high. By determining the phase diagram for an analyte with an aptamer and comparing it with the corresponding phase diagram for the analyte-antibody immunocomplex, conditions can be found that will favor the formation of the former over the latter.

Protein Refoldinq: A growing number of proteins are produced using recombinant DNA technologies. A frequent problem encountered in the commercial and research-oriented production of recombinant proteins is that overexpression of the genes encoding for the protein can lead to aggregated and non-functional protein. Overproduced proteins are often contained in inclusion bodies inside of the producing cells. Inclusion bodies are easily removed from other cell debris by means such as centrifugation or filtration and provide for rapid recovery and a powerful purification which becomes useful only when the protein can be successfully dispersed and refolded into an active form. Current procedures for refolding include addition of chaperone proteins, detergents, organic solvents or chaotropic agents such as urea or guanidinium chloride followed by dialysis to remove these agents. These processes can be time consuming and expensive when performed on a large scale.

The new methods described herein provide a method that can rapidly disrupt aggregates and allow them to refold as individual, active proteins without the use of dialysis. The method utilizes the ability of high hydrostatic pressure to strongly and rapidly disrupt aggregation and/or cause reversible protein unfolding.

The refolding reaction mixtures can include, for example, a pressure sensitive buffer and a solid phase resin. The pressure effect on the charge of the resin will be the sum of its own ionization volume and that of the buffer, allowing large changes in the charge of the resin. Such a resin and buffer system would constitute an ion exchange system which can reversibly bind and release any ionic compound.

By cycling between high and low hydrostatic pressure, the following will occur:

1) The pH of the solution will fluctuate, causing disruption of the aggregated proteins.
2) The charge on the resin will fluctuate, reversibly binding the protein molecules and catalyzing the refolding of the protein relative to re-aggregation.

A protein with a multiplicity of acidic groups would benefit from a resin/buffer system in which the resin becomes more positively charged at high pressure, whereas a protein with many basic groups would suggest the choice of a system in which the solid became more negatively charged with pressure.

Aggregated proteins that are cross-linked by disulfide bonds can be refolded, using high pressure and a pressure sensitive buffer to simultaneously denature the protein molecules and raise the pH to increase the activity of a reducing agent such as dithiothreitol. Upon lowering of the pressure, the protein can refold and be reoxidized (e.g., by air or other oxidant) to form the correct disulfide bonds.

The new method has the advantages of increasing the rate of refolding and facilitating the release of the protein from the matrix, resulting in a high concentration of folded protein.

Separation: Hyperbaric pressures can alter binding rates and affect binding affinity. Binding partners that have low affinity at atmospheric pressure can, for example, behave as high affinity partners at higher pressures. The pressure-mediated variable control of binding affinity can be used as a purification method.

For instance, contaminated mixtures containing compounds of interest can be placed in fluid contact with molecules known to bind the compounds with pressure-dependent affinity. That is, low affinity at atmospheric pressure, higher affinity at elevated pressures (association enhancement); or vice versa (dissociation enhancement). Examples are described below. To facilitate later dissociation of the binding partners and subsequent collection of the desired compound, the latter molecules can be immobilized.

In association enhancement, the pressure in the reaction vessel can be elevated before, during, or subsequent to the introduction of the desired compounds. This causes the compounds to bind tightly to the immobilized binding molecules, as unbound contaminants are flushed away with vigorous washing with fluidic liquid (e.g., solvent) or gas. In a final step, the purified compounds can be dissociated from the immobilized binding molecules at atmospheric pressure and collected at atmospheric pressure.

The association enhancement scenario is appropriate for describing protein-protein binding interactions, especially if the affinity of the proteins for each other is relatively low at atmospheric pressure. This makes the proteins involved ideal for purification by the new methods, as the affinity can potentially be increased drastically by pressure change. An illustration of a protein-protein interaction is shown in FIG. 5.

Figure 5:
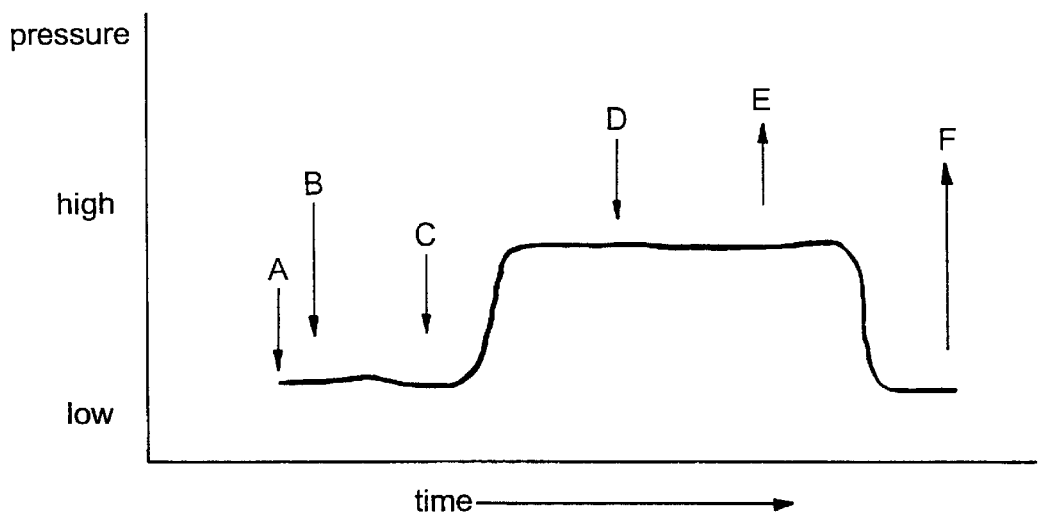
FIG. 5 is a plot of pressure against time for a separation process of the invention.

At point A in FIG. 5, one protein is immobilized on a solid phase support at low pressure. A mixture containing the other protein is introduced at point B, also at low pressure. A small amount of complex may form between the proteins (point C). However, when the pressure is raised to a higher pressure at point D, complexation is greatly enhanced. The complexes can be washed with clean solvent at point E. It is possible to wash the complexes without losing the complexes themselves because they are attached to the solid support. This step removes at least some of, and preferably most of, the contaminants. The pressure is finally lowered (point F), and one protein is separated from the other protein (point F).

In dissociation enhancement, only the final step differs. Rather than the purified compounds being dissociated from the immobilized binding molecules at atmospheric pressure, the pressure is raised to a second pressure that is high enough to cause dissociation. As described above in reference to assays, moderate pressures tend to increase binding affinity whereas still higher pressures (e.g., greater than about 30,000, or even 60,000, psi) can, for example, cause reversible (or irreversible) structure disruption of one of the binding partners, which in turn can result in dissociation. The dissociation enhancement scenario is fitting, for example, for characterizing the binding of antibodies to antigens. Antigen-antibody binding constants range from below $10^5$ $mol^{-1}$ to above $10^{12}$ $mol^{-1}$, and most typically are from about $10^8$ to $10^{10}$ $mol^{-1}$.

A number of other scenarios are also plausible. For example, temperature and pressure can be simultaneously manipulated to affect association and dissociation rates, as described above in connection with assays. Kinetic studies and pressure-temperature diagrams can also be used to assist in predicting the association and dissociation characteristics of model systems.

In still another example, contaminated mixtures containing the compounds to be isolated can be placed in fluid contact with binding molecules that bind to and exhibit pressure-dependent inhibition of enzyme catalytic activity toward the compounds (i.e., high activity at atmospheric pressure, essentially no activity at elevated pressure; high binding affinity at all pressures). In this case, the mixture can be introduced to the binding molecules at high pressures to form non-reactive binding complexes, the contaminants can be flushed away, and a reagent can be introduced to cause dissociation of the binding complex. As used above, enzyme catalytic activity refers to the ability of the enzyme to chemically convert the substrate to a product.

The latter procedure can be used, for example, for purifying the substrate of an enzyme. Enzymes bind to their substrates with great selectivity and affinity. At atmospheric pressure, a molecule of an enzyme binds to a substrate molecule and converts the substrate molecule into a product molecule. The remarkable ability of enzymes to bind to their substrates with high selectivity is generally unaffected by pressure. However, the catalytic activity of the enzymes is generally rendered inactive by high pressure conditions.

Thus, although the enzyme will still bind with great selectivity to its substrate under hyperbaric conditions, the substrate will not be converted to product. If the enzyme is immobilized by attachment to a solid support, for example, the substrate will also be immobilized, while the contaminants are being flushed away with a wash solution.

Addition of a reagent that facilitates the dissociation of the enzyme-substrate complex at the elevated pressure can allow the purified substrate to be isolated. Reagents that can be useful for such dissociation include, but are not limited to: acids; bases; salts, such as NaCl or $MgBr_2$; metal-scavengers; detergents, such as sodium dodecyl sulfate (SDS); dissociating agents; chaotropic agents, such as thiocyanate; water; organic solvents, such as dioxane, ethylene glycol, or dimethylsulfoxide; chelating agents; or other binding partners, such as metal ions. Non-chaotropic agents can also be used; examples include AFC Elution Medium (Sterogene Biochemicals) or Immunopure Gentle Ag/Ab Elution Buffer (Pierce).

Dissociation can also be effected by raising the pressure of the enzyme-substrate complexes still higher, as described above in the context of dissociation of endogenous ligands in preparation for assays. In this case, pressures that allow reversible dissociation are preferred, since the binding molecules ideally will be reused. The enzymes themselves can also be isolated in a similar manner, by using immobilized substrates to capture the enzymes present in a mixture.

Alternatively, if the goal is to isolate a relatively purified product (i.e., a substance obtained by enzymatic reaction of the substrate), rather than to isolate the substrate itself, the same procedure can again be employed, with the exception that the pressure is instead lowered after washing. Reducing the pressure to atmospheric pressure, for example, can allow the enzyme to regain its activity. The purified substrate can then be enzymatically converted to a high purity product. Enzymes typically have much lower affinity for the products than for the original substrates, so the products can be easily isolated.

Moderately high or low pressure dissociation is generally preferable to traditional elution methods (e.g., chemical methods, such as pH-controlled elution), as the traditional methods are typically harsher and can lead, for example, to irreversible structure disruption of proteins. As mentioned above, very high pressures (e.g., greater than about 100,000 psi) can also lead to irreversible structure disruption.

A contaminated mixture in the present context includes a contaminant, a material that is present but not desired in the sample. Examples of contaminants include byproducts from the manufacture of the desired compound, degradation products of the desired compound, catalysts, impurities contained in natural or commercial materials, and residual high-boiling solvent.

In most cases, there can be two or more binding components in a mixture, one of which can be of lower molecular weight and size and can be a peptidic ligand, an antigen, or a nucleic acid probe, for example. The other partner can be a receptor, an antibody, or target DNA or RNA, or other molecules that bind to the first compound. Either component can play either role; thus, in the examples given above, either the ligand or the receptor, the antigen or the antibody, or the probe or the target can be the desired compound to be purified. The other component would preferably be present in the form of a binding molecule immobilized on a solid support or membrane.

Both the contaminated compound to be purified and the immobilized binding molecules are dissolved in, suspended in, or mostly surrounded by a fluid. The fluid can be a liquid (e.g., acidic, neutral, or basic aqueous or organic solvents, or solutions thereof), a gas (e.g., an inert gas or a noble gas), or even a supercritical fluid.

Binding molecules can be immobilized to a solid support, such as a particle, a solid or hollow polymer bead, a well, a tube or column, a strip, a molded material, a polymer matrix, a semipermeable, porous or nonporous membrane in the form of a filter or bag, or other support material. Solid supports made of various polymers in many physical configurations and with activated or specifically reactive surfaces are commercially available for use in research, diagnostic, and bioseparation products. Numerous methods for covalently immobilizing ligands or binding proteins to surfaces are described in "Affinity Chromatography: Bioselective Adsorption on Inert Supports" by William J. Scouten, Wiley-Interscience (1981). The binding of the molecule to the solid support is often achieved through passive adsorption, where the reactant and surface allow such manipulation, or by chemical (covalent) linkage to a specific reactive group on the surface. Non-limiting examples of contaminants and compatible supports are provided in Table 1.

TABLE 1

| Contaminant Type | Example | Immobilized Binder |
|---|---|---|
| pyrogens | endotoxins, lipopolysaccharides | histidine |
| proteolytic enzymes carrier | endoproteases | $\alpha_2$-macro-globulin, fixed |
| detergents | triton-X100, or sodium dodecyl sulfate | BioBeads SM-2 isolation |
| process lipids | lipoproteins | Lipidex 1000 |
| heavy metals | mercury | organic thiols |
| viruses | hepatitis B virus | octanoic acid hydrazide |

The phrase "bound complex" refers to the actual combination of the desired compounds and the immobilized binding molecules. These binding complexes are often named by their components. For example, if A is a ligand and B is a receptor, the binding complex can be represented as [AB]. Preferably, the complexes described herein are dissociably linked, meaning that the complex formation is reversible. Generally, the linkage is electrostatic (e.g., via hydrogen bonds, van der Waals forces, or ionic bonds), although it can be covalent. In most cases, the reverse process (i.e., dissociation) can be induced by further varying the pressure or by adding a reagent.

The following examples will illustrate the invention, but they do not limit it. Examples 1–5 are rophetic examples; 6–10 are actual examples.

EXAMPLE 1

Pressure Modulation and Solid-phase Immunosorbant Used to Prepare Serum Sample for Assay of HIV p24

Step 1: Immobilizing Immunosorbent on the Tube Wall.

Into polypropylene tubes, approximately sized for the pressure device, is dispensed 100 $\mu$l of a 5 to 10 $\mu$g/ml dilution of prepurified recombinant HIV-1 p24 (obtained from Immunodiagnostics, Inc., Bedford, Mass.) in 0.1 M potassium carbonate buffer, pH 9.3. This mixture is allowed to incubate overnight in a refrigerator at 2–8° C. The solution is decanted, and 100 $\mu$l of 2% Bovine Serum Albumin solution in PBS (0.05 M Phosphate buffered saline, pH 7.4, PBS) is added. This resulting mixture is decanted and a second addition of the same solution is added and allowed to block the walls of the container for at least two hours at room temperature. The solution is decanted and the tubes are inverted and allowed to dry at room temperature. They are stored at 2–8° C. in tightly sealed plastic bags containing added desiccant to assure dryness.

Step 2: Sample Preparation

Into the containers described in Step 1 is added 50 $\mu$l of serum sample to be tested. An identical volume of either PBS or PBS containing an appropriate dissociation accelerant (e.g., glycine-HCL, pH 2.5, urea, or a water miscible, organic solvent), is added with mixing. The tubes are sequentially inserted into the hyperbaric device and the pressure raised to 50,000 psi for a suitable period. The tubes are allowed to return to atmospheric pressure and incubated at room temperature for at least two hours to assure that the endogenous binder in the sample will be competitively bound by the large excess of immobilized antigen on the internal wall of the tubes. An aliquot of the binder-depleted sample is now removed for conventional determination of HIV p24.

EXAMPLE 2

Use of Particulate Format Immunosorbent

Step 1: Preparation of Latex Immunosorbent

A bulk preparation of HIV-1 p24 adsorbed latex particles is prepared by following the procedure recommended by Bangs Laboratories (Carmel, Ind.). The resultant suspension is stored refrigerated at 2–8° C. until use.

Step 2: Sample Preparation

Into polypropylene tubes, approximately sized for the pressure device, is dispensed 100 $\mu$l of the Latex immunosorbent and 50 $\mu$l of each sample to be tested. The tubes are sequentially inserted into the hyperbaric device and the pressure raised to 50,000 psi for an appropriate period. The tubes are allowed to return to atmospheric pressure and incubated at room temperature for at least two hours to assure that the endogenous binder in the sample will be competitively bound by the large excess of immobilized antigen on the latex particles. The tubes are rapidly spun at approximately 2,000 xg to sediment the particles. An aliquot of the binder-depleted sample is now removed for conventional testing.

EXAMPLE 3

Pressure Modulation and Size Fractionation Used to Prepare Serum Sample for Assay of HIV D24

Step 1: Size Fractionation Devices

Micro-sized gel filtration columnar devices from Pharmacia are prepared just before use by passing approximately one ml of PBS through.

Step 2: Sample Preparation

Polypropylene tubes, approximately sized for the pressure device, each containing 50 $\mu$l of a sample to be tested are subjected to the pressure as in Example 1 and immediately flash frozen. The sealed base of each tube is sequentially cut open and the resultant bottomless tubes are placed into the gel filtration columnar devices and allowed to thaw. Without delay, cold (4° C.) PBS is flowed through the tubes into the resin bed at the rate recommended by the device manufacturer and collection is initiated. The first fraction, containing the large antibody portion, is discarded and the second HIV-1 p24 fraction is collected and assayed in the conventional manner.

EXAMPLE 4

Determination of a Pressure-temperature Phase Diagram of Antigen-antibody Reactivity for the HIV gag D24:Rabbit Anti-D24 Pair The following procedure illustrates the creation of data for producing a phase diagram as described above. The specific illustration involves recombinant HIV (HIV-1 bS) gag p24 and rabbit anti-p24.

Materials

A solid phase immunosorbent for antibody to HIV-1 gag p24 was prepared by coating polystyrene microliter plates (HiBind, Corning/Costar, Cambridge, Mass.) with a one $\mu$g/ml suspension of recombinant HIV-1 IIIB p24

(ImmunoDiagnostics, Inc, Bedford, Mass.) overnight at 4° C. in NaHCO$_3$, pH 9.2. Unreacted sites were blocked with SuperBlock in PBS or Tris (Pierce Chemical, Chicago, Ill.).
Experimental Method.

Recombinant HIV-1 IIIB gag p24 and rabbit anti-p24 HIV-1 IIIB IgG were incubated together to form samples of immune complexes. A sample was placed in a deformable plastic capsule, and overlaid with melting point bath oil (Sigma, St. Louis, Mo.). The capsule was placed in a device for generating high pressures (HiP, Erie, Pa.). While pressure was applied to an aliquot of the immune complex, a parallel sample was subjected to the same temperature conditions at atmospheric pressure. After release of high pressure, the sample and a parallel (no pressure pretreatment) control was placed in wells of the p24 coated microplate. The level of free antibody (uncomplexed with antigen) in samples was quantified by reacting samples in the microtiter plates for one hour at ambient temperature, then detecting the captured antibody with an HRP-labelled second antibody. The degree of complexation of the pressure treated and control samples was determined from a standard curve compiled using varying amounts of the preformed immune complex, p24, and anti-p24 antibody such that the concentration of p24 and anti-p24 was constant in each measurement. Dissociation or additional association of the antibody:antigen complex translates respectively to an increase or decrease in signal intensity in the assay.

EXAMPLE 5

High Throughput Screening of Phage Display of Mutant Proteins

A pressure-modulation apparatus which is capable of introducing, reacting, and removing fluids from a reaction chamber while under high pressure has been described and referenced in PCT/US96/03232. This apparatus is fitted with a modified reaction chamber that enables real-time detection and monitoring of biomolecular binding interactions. An example of this type of chamber includes, for external spectrometry, an optical window (e.g., sapphire), or, for internal spectrometry, a fiber optic bundle in direct contact with internal fluids and targeted against an internal viewing plane. Another example of an internal detection sensor is an electrochemical detection probe.

In an example of a phage display technique, the phage host (e.g., transformed E. coli cells) expresses gene III capsid protein of phage and the corresponding target protein as a fusion protein on its surface. Each phage moiety is labeled with a reporter molecule (e.g., a radioactive dye, etc.) or has a chemical structure that enables detection, e.g., native fluorescence.

The target protein binds to a previously immobilized target receptor molecule on a solid support, which then screens the phages. The screening of the expressed phage mutants, each with different gene III-antibody fusion proteins, is based on affinity. Serial introduction of the phage library into the reaction chamber, modulation of the pressure, and observation of the real-time binding rate and affinity of interaction using laser-induced excitation and emission of fluorescence spectra allow the determination of phage binding characteristics.

Following affinity analysis and characterization, the phage is removed from the reaction chamber by pressure modulation to dissociate the biomolecular stereoelectronic interactions. This procedure may either enhance or perturb binding depending upon the volume change associated with activation. In either case, a second phage is then introduced for affinity analysis and characterization. The pressure-modulated association and dissociation of complexes enables rapid screening. This serial process can be modified for parallel screening.

EXAMPLE 6

Use of High Hydrostatic Pressure to Accelerate Antigen-antibody Binding

The use of high hydrostatic pressure to accelerate the rate of binding of an antibody to an antigen was demonstrated using recombinant HIV-1 IIIB gag p24 and rabbit anti-p24 HIV-1 IIIB IgG. A pressure of 60,000 psi (420 MPa) applied for 10 minutes at ambient temperature (~22° C.) resulted in a level of binding equivalent to the binding noted after at least four hours at atmospheric pressure. A 10 minute application of 30,000 psi (210 MPa) pressure resulted in binding equivalent to 30 minutes at atmospheric pressure. At 20,000 psi (140 MPa), 10 minutes of pressure application produced only marginal effects on binding, relative to atmospheric pressure. The details of the experimental protocol follow.

125 µl of 0.2 ng/µl recombinant HIV-1 IIIB gag p24 antigen (ImmunoDiagnostics, Inc., Bedford, Mass.) was added to 125 µl of 2 ng/µl rabbit anti-p24 HIV-1 IIIB IgG antibody (ImmunoDiagnostics, Inc.) in phosphate buffered saline (PBS), pH 7.4 in a polypropylene microfuge tube, such that 100 µl of the antigen/antibody mixture contained about 10 ng of antigen and about 100 ng of antibody. 120 µl of the reagent mixture was inserted into a deformable plastic capsule and overlaid with melting point bath oil (Sigma, St. Louis, Mo.). The capsule was immediately placed in the reaction chamber of a high pressure apparatus (HiP, Erie, Pa.), maintained at ambient temperature and the pressure was then raised to the desired elevated level (i.e., as indicated in the previous paragraph) using a manually operated piston.

Control samples, in which either the antibody or the antigen was omitted, were also subjected to the same experimental conditions. All experiments were performed at ambient temperature. A solid phase immunosorbent ELISA assay for detecting antibody to HIV-1 gag p24 was developed in-house. Polystyrene microtiter plates (HiBind, Corning/Costar, Cambridge, Mass.) were coated with a 1 µg/ml suspension of recombinant HIV-1 gag p24 antigen overnight at 4° C. in aqueous NaHCO$_3$, pH 9.2. Unreacted sites were blocked with SuperBlock® in PBS-Tris (Pierce Chemical, Chicago, Ill.).

After elevated pressure had been applied for the desired time, test samples were measured using the p24-coated microwell ELISA assay: A 100 µl aliquot of the test sample was immediately removed from the capsule and placed in a well of the p24-coated microplate; 100 µl of the nonpressurized test solution was tested in parallel. Test samples were shaken at ambient temperature in the microtiter wells for one hour, then washed three times with PBS-0.05% Tween-20 (PBS-T). Antibody binding to the immobilized p24 antigen was detected using goat anti-rabbit IgG conjugated to horseradish peroxidase (HRP) (Pierce Chemical), and the HRP substrate 2,2'-azido-bis(3-ethylbenzothiazoline)-6-sulfonic acid diammonium salt (ABTS).

The microplates were shaken at ambient temperature with 100 µl of a 1:2,500 dilution of the goat anti-rabbit HRP conjugate, then the microtiter plate wells were washed five times with PBS-T. 100 µl of ABTS was added, and the plates were analyzed in a spectrophotometer at 405 nm after a 30 minute incubation.

To select appropriate reagent concentrations for experiments at high pressure, an initial study was performed at atmospheric pressure, using various ratios of antibody to antigen. Antibody and antigen were mixed in polypropylene microfuge vials, then held overnight at 4–6° C. to reach equilibrium binding prior to measurement in the ELISA assay. This study showed that 100 ng of the anti-p24 antibody alone (i.e., with no p24 antigen) resulted in an absorbance value of approximately 1.1 OD at 405 nm, and (ii) binding of 10 ng of p24 antigen to the antibody during the overnight incubation resulted in close to maximal inhibition of the subsequent binding of the antibody to the p24 antigen immobilized on the microtiter plate.

Based on the initial data described above, the kinetics of binding at atmospheric pressure were determined in mixtures containing 100 ng of antibody and 10 ng of antigen per 100 µl. The antigen/antibody mixtures were incubated for different times at ambient temperature, and then subjected to the ELISA assay. The absorbance values measured in the ELISA assay were used to calculate the extent of the binding of the p24 antigen with the anti-p24 antibody using the antibody-only sample (highest absorbance) as zero binding and the overnight incubation of the antigen with the antibody (lowest absorbance) as 100% binding.

Figure 6:
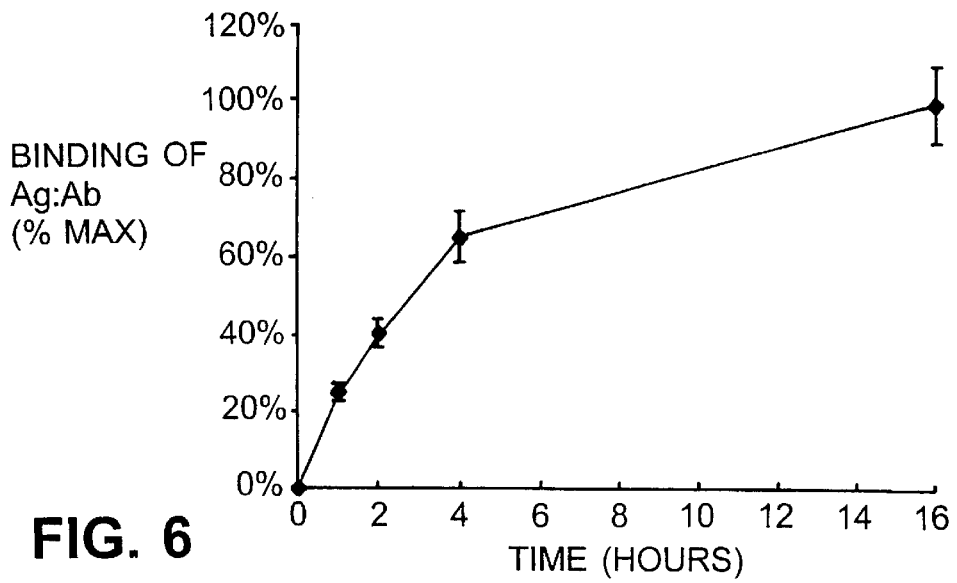
FIG. 6 is a plot of p24: anti-p24 antigen:antibody binding as a function of time at atmospheric pressure at ambient temperature.

As shown in Table 2 and FIG. 6, in a typical experiment conducted at atmospheric pressure and ambient temperature, approximately 25% binding between antigen and antibody occurred in one hour; 40% in two hours; and 65% in four hours. Experiments to determine the effect of high pressure on the binding of anti-p24 antibody to p24 antigen were then commenced. Preincubation of the anti-p24 antibody alone (without the p24 antigen) at 60,000 psi for 10 minutes did not result in any discernible decrease in the absorbance, indicating that pressures up to 60,000 psi did not affect the ability of the antibody to subsequently bind to the antigen.

TABLE 2

Time course of the binding of p24 antigen to
anti-p24 antibody at atmospheric pressure

| Time (hours) | Binding (% max) |
|---|---|
| 1 | 25 |
| 2 | 40 |
| 4 | 65 |
| 16 | 100 |

Figure 7:
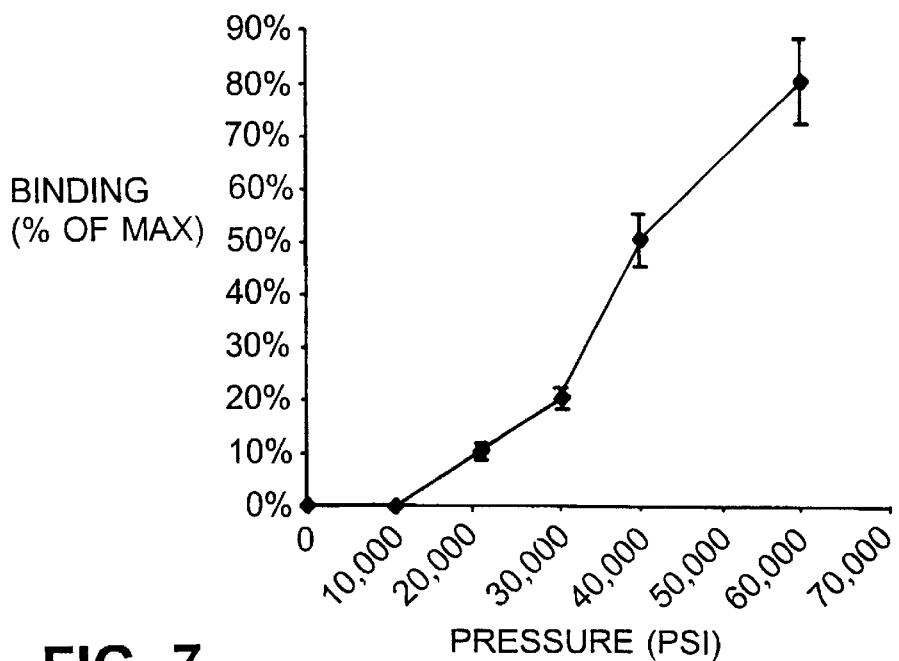
FIG. 7 is a plot of p24: anti-p24 antigen:antibody binding as a function of pressure for 10 minutes at ambient temperature.

Table 3 and FIG. 7 show binding (±10%) of antigen with antibody as a function of pressure applied for 10 minutes. At 10,000 psi, no pressure effect was evident; approximately 10% binding was observed at 20,000 psi; 20% at 30,000 psi, 50% at 40,000 psi; and 80% at 60,000 psi.

TABLE 3

Effect of pressure (10 minutes) on the binding of
p24 antigen to anti-p24 antibody

| Pressure (psi) | Binding* (% max; ±10) |
|---|---|
| 14 (1 atm) | 0 |
| 10,000 | 0 |
| 20,000 | 10 |
| 30,000 | 20 |
| 40,000 | 50 |
| 60,000 | 80 |

*max = 100%, observed in overnight incubations at 4–6° C.

Figure 8:
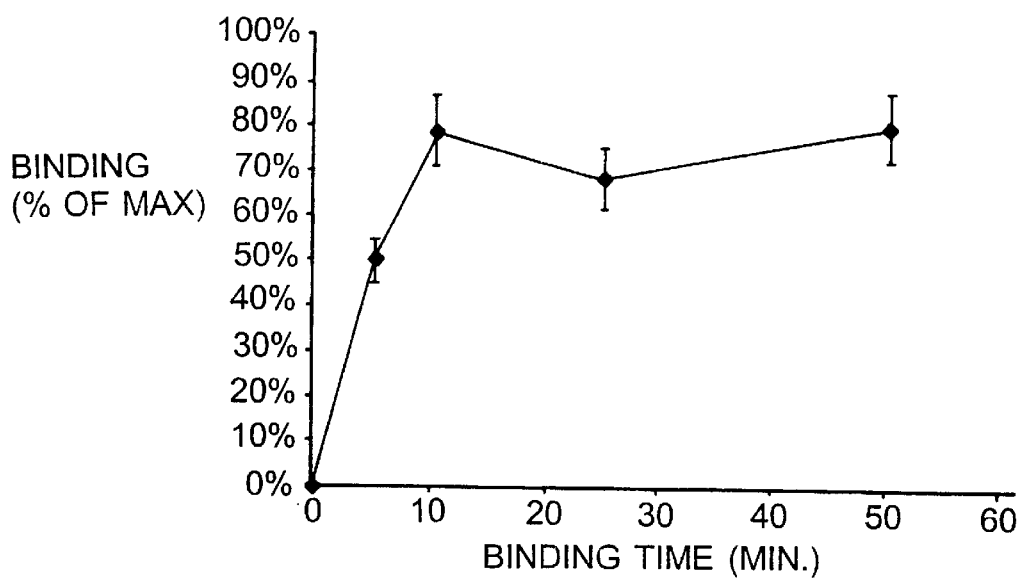
FIG. 8 is a plot of p24: anti-p24 antigen:antibody binding as a function of time at 60,000 psi at ambient temperature.

Table 4 and FIG. 8 show the effect of applying 60,000 psi for different durations on the binding of antigen to antibody (the solid circles indicate enhancement). The

TABLE 4

Effect of 60,000 psi on the binding of p24 antigen to anti-p24 antibody

| Binding Time (minutes) | Binding* (% max; ±10) |
|---|---|
| 0 | 0 |
| 5 | 50 |
| 10 | 75 |
| 25 | 69 |
| 50 | 82 |

*max = 100%, observed in overnight incubations at 4–6° C.

data indicate that enhancement of binding occurs rapidly at 60,000 psi, with 50% binding in 5 minutes. The other data points correspond to 79% (±10%) at 10 minutes; 69% (±10%) at 25 minutes; and 82% (±10%) at 50 minutes, showing that saturation binding was reached in 10 minutes. The data point marked with a solid square shows binding achieved at atmospheric pressure after 60 minutes.

EXAMPLE 7

Use of High Hydrostatic Pressure to Disrupt an Antigen-antibody Complex

The use of high hydrostatic pressure to disrupt an antibody:mucin glycoprotein immune complex was demonstrated in a model system. The antibody was bound to a mucin glycoprotein immobilized in microtiter plate wells. High pressure was applied to the microwells in a custom designed high pressure chamber. Dissociation of antibody from the immobilized antigen was monitored by ELISA assays.

A solid phase immunosorbent ELISA assay for detecting a mouse monoclonal IgM antibody to a mucin glycoprotein was developed in-house. Polystyrene microtiter plates (HiBind, Corning/Costar, Cambridge, Mass.) were coated with 0.1 ml of epiglycanin at 100 ng/ml overnight at 4° C. in phosphate buffered saline (PBS), pH 7.4. Unreacted sites were blocked for one hour with SuperBlock in PBS (Pierce Chemical, Chicago, Ill.).

The mouse monoclonal antibody was then bound to the immobilized antigen by incubating microwells with 0.1 ml of 100 ng/ml antibody in PBS, pH 7.4 for one hour with shaking at ambient temperature, (~22° C.). After washing five times with PBS-0.05% Tween-20 (PBS-T), the bound antibody was incubated with goat anti-rabbit conjugated to horseradish peroxidase (HRP) (Pierce Chemical). After five more washes in PBS-T, 100 µl of ABTS was then added, and the plates were analyzed in a spectrophotometer at 405 nm, after a one hour incubation.

To determine the effect of pressure on the binding of the antibody, microwells with immobilized antigen and bound antibody were overlaid with melting point bath oil (Sigma, St. Louis, Mo.), then inserted into the reaction chamber of a custom designed high pressure apparatus attached to a manually operated pressure apparatus (HiP, Erie, Pa.). Elevated pressure was applied for 20 minutes to a microwell. Parallel control samples were overlaid with oil and held at atmospheric pressure during the application of high pressure to the test sample. All experiments were performed at ambient temperature.

After the elevated pressure had been applied for the desired time, the test solutions were immediately transferred to a second set of microwells to measure the level of dissociated antibody, using the ELISA assay described above. The pressurized and parallel control microwells were also washed with PBS-T, and tested for retained antibody using the same ELISA procedure.

Pressures of 20,000, 40,000, 60,000, and 80,000 psi resulted in reductions in the absorbance values in the ELISA assays in which the level of antibody retained in microwells was measured after the application of high pressure. Absorbance reductions were in the range 37% (±15%). Application of 60,000 psi to the immobilized glycoprotein only (in the absence of antibody) did not result in any subsequent decrease in absorbance in the ELISA assay. These data thus indicated that application of pressures ranging from 20,000 to 80,000 psi (140 to 560 MPa) caused the dissociation of antibodies from the immobilized mucin glycoprotein.

The effect of the elevated pressure on the subsequent immunoreactivity of the dissociated antibodies was revealed by assaying the supernatants in a separate ELISA assay in which the supernatants of the pressurized wells were assayed for dissociated antibodies. Antibodies that had been dissociated at 20,000 psi and 40,000 psi were able to rebind to the immobilized mucin glycoprotein, indicating that the effect of these pressures on the binding of the immune complex was reversible. In contrast, antibodies that had been dissociated at 60,000 psi and 80,000 psi did not rebind to the solid phase, indicating that pressure at these higher levels had caused irreversible disruption of the antibody structure.

EXAMPLE 8

Use of Pressure Modulation to Effect Immunoseparation in Flow System

A mucin glycoprotein, epiglycanin (EPGN), was immobilized to the inner surface of "breakaway" wells of a conventional microtiter plate in PBS at pH 7.4. The inner surface of the wells was then blocked with bovine serum albumin (BSA) in PBS. A small hole was drilled into the bottom of the microwell, which was then placed in the reaction chamber of a high pressure flow-through apparatus, such as that described in PCT/US96/03232, incorporated by reference. The reaction chamber had an internal volume of about 0.1 ml.

A solution of BSA in PBS was pumped through the reaction chamber at a pressure of about 7,000 psi with the intent to coat the inner surfaces of the system with BSA and to prevent subsequent non-specific binding of other proteins.

An IgM mouse monoclonal antibody (AE3; 1 mg/ml) with immunospecificity for EPGN was mixed with BSA (1 mg/ml) in PBS. 1 ml of the solution was pumped through the reaction chamber at a pressure of about 7,000 psi.

The entry and exit valves of the reaction chamber were closed. The 7,000 psi pressure was applied for 10 minutes to try to achieve enhanced binding of the AE3 antibody to the EPGN immobilized on the solid phase. The entry and exit valves were then opened, and 1 ml of PBS was pumped through the reaction chamber, again at 7,000 psi to wash out the system. Antibodies that had been captured through pressure-enhanced affinity binding to the EPGN were retained on the solid phase.

Next, a pressure of 20,000 psi was applied to the PBS solution. The entry and exit valves were closed again, The 20,000 psi pressure was applied for 10 minutes. The entry and exit valves were then opened once again. Additional PBS solution was pumped through the reaction chamber at 20,000 psi, as 0.1 ml fractions were collected and assayed by the ELISA assay described in the previous example. Fractions containing antibodies, which had been first captured on the solid phase during application of the 7,000 psi pressure and then dissociated from the binding partners by application of the 20,000 psi pressure, were identified by increased absorbance readings using the ELISA described below.

Control samples were pumped through the high pressure apparatus at atmospheric pressure. All experiments were conducted at ambient temperature.

A solid phase immunosorbent ELISA assay for detecting a mouse monoclonal IgM antibody to a mucin glycoprotein was developed in-house by standard methods. Polystyrene microtiter plates (HiBind, Corning/Costar, Cambridge, Mass.) were coated with 0.1 ml of epiglycanin at 100 ng/ml overnight at 4° C. in phosphate buffered saline (PBS), pH 7.4. Unreacted sites were blocked for one hour with SuperBlock in PBS (Pierce Chemical, Chicago, Ill.). The mouse monoclonal antibody was then bound to the immobilized antigen by incubating microwells with 0.1 ml of 100 ng/ml antibody in PBS, pH 7.4, for one hour with shaking at ambient temperature. After washing five times with PBS-0.05% Tween-20 (PBS-T), the bound antibody was incubated with goat anti-rabbit conjugated to horseradish peroxidase (HRP) (Pierce Chemical). After five more washes in PBS-T, 100 µl of ABTS was then added. After a one hour incubation time, the plates were read at 405 nm.

Pressure of 7,000 psi resulted in accelerated binding of the antibody to the immobilized antigen. After capture of the antibody at 7,000 psi, subsequent application of a pressure of 20,000 psi resulted in the dissociation of antibody from the solid phase. That the dissociated antibody was still immunoreactive was shown by ELISA assay.

EXAMPLE 9

High Pressure Mediated Dissociation of a PSA Immune Complex

A solid phase immunosorbant ELISA assay for detecting antibodies to prostate specific antigen (PSA) was developed in-house. Polystyrene microtiter plates (HiBind, Corning/Costar, Cambridge, Mass.) were coated overnight at 4° C. with 0.1 ml of PSA (Sigma Chemicals, St. Louis, Mo.), at concentrations ranging from 625 to 1,265 ng/ml in phosphate buffered saline (PBS), pH 7.4. Unreacted sites were blocked for one hour with SuperBlock in PBS (Pierce Chemical, Chicago, Ill.). An anti-PSA mouse monoclonal antibody (DRG International, Mountainside, N.J.) was then bound to the immobilized antigen by incubating the antigen-coated microwells with 0.1 ml of anti-PSA antibody (78–312 ng/ml) in pH 7.4 PBS overnight at 4° C. The wells were then washed five times with PBS-0.05% Tween-20 (PBS-T). To determine the level of anti-PSA antibody bound to immobilized PSA, wells were reacted with goat anti-mouse IgG (H+L) conjugated to horseradish peroxidase (HRP) (Pierce Chemical, Chicago, Ill.). After five more washes in PBS-T, 100µl of ABTS was then added, and the plates were read at 405 nm after one hour incubation.

To determine the effect of pressure on the binding of the antibody to the PSA antigen, 0.1 ml of SuperBlock in PBS (Pierce Chemical, Chicago, Ill.) was added in microwells in which anti-PSA antibody had been bound to immobilized PSA. The microwells were then overlaid with melting point bath oil (Sigma, St. Louis, Mo.) and inserted, at atmospheric pressure, into a custom designed high pressure chamber attached to a manually operated pressure apparatus (HiP, Erie, Pa.). High pressure was then applied for 30 minutes to each microwell. Dissociated antibody was collected into the PBS medium. Parallel control samples were overlaid with oil and maintained under ambient conditions during the application of high pressure to the test sample. After high pressure had been applied for the desired time, the test solutions were immediately transferred to a second set of microwells containing immobilized PSA. The level of dissociated antibody was measured using the ELISA assay described above. The pressurized and parallel control microwells were also washed with PBS-T and tested for retained antibody using the same ELISA procedure.

The absorbance of a sample pressurized at 60,000 psi and 40° C. was 0.937, whereas the absorbance of the unpressurized control was 1.457. Dissociation of anti-PSA from PSA was confirmed in the absorbance values of the supernatant. The absorbance of the supernatant of the pressurized well was 0.504, while the absorbance of control held at atmospheric pressure was 0.113. A decrease in the absorbance of a pressurized microwell relative to its respective control is consistent with pressure-induced dissociation of anti-PSA antibody from immobilized PSA. The dissociation is confirmed if the supernatant removed from the pressurized well shows an increase relative to the atmospheric control.

Raising the temperature to 40° C. during application of pressure significantly enhanced dissociation of anti-PSA from PSA. The combination of 80,000 psi and 21° C. resulted in the absorbance of the pressurized well decreasing from 1.556 to 1.052. In contrast, the combination of 80,000 psi and 40° C. resulted in the absorbance decreasing 1.458 to 0.733. The higher level of absorbance decrease in the later case was consistent with a higher level of dissociation under those conditions. This interpretation of the data was confirmed by the absorbance values measured in the supernatant. The absorbance value of the 80,000 psi/40° C. pressurized supernatant was 0.629 while the absorbance of the control was 0.248.

EXAMPLE 10

Procedure for Determining the Phase Diagram Corresponding to the Binding of an Aptamer to a Protein The aptamer derived by in vitro transcription of Sequence 26B according to the method of Tuerk et al. (*Science*, 249:505–510, 1990) was labeled with biotin by including a low level of biotin-16-UTP in the bacteriophage T7 RNA polymerase reaction, using the biotin RNA labeling mix manufactured by Boehringer Mannheim (Indianapolis, Ind.). A solid phase absorbent for the aptamer was prepared by incubating polystyrene microtiter plates (HiBind, Corning/Costar, Cambridge, Mass.) with a 1 µg/ml solution of bFGF (Bachem, Torrance, Calif.) overnight at 4° C. in $NaHCO_3$, pH 9.2. Unreacted sites were blocked with Superblock in PBS (Pierce Chemical, Chicago, Ill.).

bFGF and the biotinylated aptamer 26B were incubated together to form samples of complexes. A sample was placed in a deformable plastic capsule and overlaid with melting bath oil (Sigma, St. Louis, Mo.). The capsule was placed in a device for generating high pressures (HiP, Erie, Pa.). While pressure was applied to an aliquot of the complex, a parallel sample was subjected to the same temperature conditions at atmospheric pressure. After release of the high pressure, the sample and the parallel control (i.e., no pressure pretreatment) were placed in wells of bFGF coated microplate. The level of free aptamer (uncomplexed with bFGF) was quantified by reacting samples in the microtiter plates for one hour at ambient temperature, then detecting the captured aptamer with HRP-labeled streptavidin (Sigma, St. Louis, Mo.). The degree of complexation of the pressure-treated and control samples was determined from a standard curve compiled using varying amounts of the preformed bFGF-aptamer complex and the biotinylated 26B aptamer such that the concentration of bFGF and aptamer was constant in each measurement. Dissociation or additional association of the bFGF-aptamer complex translates respectively into an increase or decrease in signal intensity in the assay.

Other Embodiments

From the description above, one skilled in the art can ascertain the essential characteristics of the invention and without departing from the spirit and scope thereof, can make various changes and modifications of the invention to adapt it to various usages and conditions. All references cited herein are incorporated by reference.

It is to be understood that while the invention has been described in conjunction with the detailed description thereof, that the foregoing description is intended to illustrate and not to limit the scope of the appended claims. Other aspects, advantages, and modifications are within the scope of the following claims. For example, a well prebound with immobilized antigen-antibody complex that could then be dissociated under pressure is also within the scope of the claims.

What is claimed is:

1. A method of assaying for an analyte, the method comprising:
   a) providing a sample, wherein the sample comprises an endogenous complex between the analyte and an endogenous sample component;
   b) subjecting the sample to an elevated pressure sufficient to dissociate the analyte from the endogenous sample component; and
   c) detecting or measuring the dissociated analyte by reacting the dissociated analyte with an exogenously supplied specific binding reagent and determining complexation between the analyte and the binding reagent.

2. The method of claim 1, wherein said assay step is carried out at a pressure intermediate between atmospheric pressure and said elevated pressure.

3. The method of claim 1 in which the pressure is high enough to irreversibly dissociate the analyte from endogenous sample component.

4. The method of claim 3 in which the assay step is performed without first separating the endogenous sample component from the analyte.

5. The method of claim 1 in which dissociation step reversibly dissociates the analyte from the endogenous sample component.

6. The method of claim 5 comprising a step, performed after the dissociation step, in which analyte is separated from the endogenous sample component.

7. The method of claim 6 in which analyte is immobilized in a chamber, and the endogenous sample component is removed from the chamber.

8. The method of claim 6, wherein the step in which analyte is separated from the endogenous sample component comprises the use of a semipermeable membrane, and
   wherein the analyte, but not the endogenous sample component, is capable of passing through the membrane.

9. The method of claim 7 in which the chamber is part of an apparatus which further comprises a valved inlet connecting the chamber to a pressurized supply area, a valved outlet connecting the chamber to a collection area, and controllers to operate the valved inlets and outlets, and the method comprises flushing analyte out of the chamber and into the collection area by introducing material from the pressurized supply area, after the endogenous sample component is removed.

10. The method of claim 1 in which the analyte is an antigen, and the endogenous sample component is a sample antibody that complexes with the antigen.

11. The method of claim 1 in which the analyte is an antibody, and the endogenous sample component is an antigen that complexes with the antibody.

12. The method of claim 1 in which the dissociation step comprises subjecting the sample to pressure in excess of 15,000 psi for a period of at least 25 milliseconds.

13. The method of claim 12 in which the dissociation step comprises subjecting the sample to pressure in excess of 30,000 psi.

14. The method of claim 1 in which the dissociation step further comprises subjecting the sample to a structure disrupting agent.

15. The method of claim 14 in which the structure disrupting agent is DTT.

16. The method of claim 15 in which the structure disrupting agent is a water miscible solvent.

17. The method of claim 1 in which the dissociation step comprises subjecting the sample to reagent that reduces or prevents reassociation of analyte and endogenous sample component, selected from the group consisting of a chelating agent, a detergent, and a chaotrope.

18. The method of claim 17 wherein the reagent is selected from the group consisting of EDTA, EGTA, o-phenanthroline, urea, and thiocyanate.

19. The method of claim 1 in which the analyte is an HIV antigen and the sample is a human bodily fluid comprising anti-analyte antibody.

20. The method of claim 1, wherein said dissociation step further comprises association of an exogenous binding partner.

21. The method of claim 20, wherein said exogenous binding partner comprises an aptamer.

22. The method of claim 1, comprising both detecting and measuring the dissociated analyte.

* * * * *